US007087396B2

(12) United States Patent
Tominaga et al.

(10) Patent No.: US 7,087,396 B2
(45) Date of Patent: Aug. 8, 2006

(54) MONOCLONAL ANTIBODY AND METHOD AND KIT FOR IMMUNOASSAY OF SOLUBLE HUMAN ST2

(75) Inventors: Shin-ichi Tominaga, 1-3-24, Edahigashi, Tsuzuki-ku, Yokohama-shi, Kanagawa, 224-0004 (JP); Takao Arai, 5-18-7, Kasuga-cho, Nerima-ku, Tokyo179-0074 (JP); Kenji Kuroiwa, Numazu (JP); Katsuhisa Oshikawa, Kawachi (JP)

(73) Assignees: Medical Biological Laboratories Co., Ltd., Nagoya (JP); Shin-ichi Tominaga, Yokohama (JP); Takao Arai, Tokyo (JP)

( * ) Notice: Subject to any disclaimer, the term of this patent is extended or adjusted under 35 U.S.C. 154(b) by 0 days.

(21) Appl. No.: 10/243,949

(22) Filed: Sep. 16, 2002

(65) Prior Publication Data

US 2003/0124624 A1    Jul. 3, 2003

Related U.S. Application Data

(63) Continuation of application No. PCT/JP00/08723, filed on Dec. 7, 2000.

(30) Foreign Application Priority Data

Mar. 21, 2000    (JP)    ............................. 2000-077383

(51) Int. Cl.
*C07K 16/28* (2006.01)
*C12N 5/20* (2006.01)
*G01N 33/543* (2006.01)
*G01N 33/535* (2006.01)
*G01N 33/577* (2006.01)

(52) U.S. Cl. ...................... 435/7.94; 435/7.1; 435/7.2; 435/7.21; 435/7.24; 435/7.9; 435/7.92; 435/70.21; 435/452; 435/332; 435/334; 435/343.2; 435/975; 436/518; 436/524; 436/528; 436/529; 436/548; 530/388.2; 530/388.22; 530/388.7; 530/388.75; 530/391.1; 530/391.3

(58) Field of Classification Search ................ 435/7.1, 435/7.2, 7.21, 7.24, 7.9, 7.92, 7.94, 70.21, 435/452, 332, 334, 343.2, 975; 436/518, 436/524, 528, 539, 548; 530/388.2, 388.22, 530/388.7, 388.75, 389.6, 391.1, 391.3
See application file for complete search history.

(56) References Cited

U.S. PATENT DOCUMENTS 4,376,110 A * 3/1983 David et al. .................... 435/5
6,399,748 B1 * 6/2002 Werenskiold ............. 435/7.94

FOREIGN PATENT DOCUMENTS

WO    WO 98/43090    10/1998

OTHER PUBLICATIONS

Ken Yanagisawa et al.; J. Biochem.; vol. 121, No. 1, pp. 95-103, 1997. See PCT search report.
F. P. Heinzel et al.; J. Exp. Med.; vol. 169, pp. 59-72, 1989. Discussed in the spec.
L. N. Araya et al.; The Journal of Immunology; vol. 143, pp. 3330-3337, 1989. Discussed in the spec.
K. Yanagisawa et al.; Federation of European Biochemical Societies; vol. 318, No. 1, pp. 83-87, 1993. Discussed in the spec.
English summary of JP-A-6-178687, date Jun. 28, 1994. Discussed in the spec. and Figure 4.
D. Xu et al.; J. Exp. Med., vol. 187, No. 5, pp. 787-794, 1998. Discussed in the spec.
M. Lohning et al.; Proc. Natl. Acad. Sci., USA, vol. 95, pp. 6830-6935, 1998. Discussed in the spec.
K. Yoshida et al.; Hybridoma, vol. 14, No. 5, 1995. Discussed in the spec.
Shin-ichi Tominaga et al.; Biochimica et Biophysica.Acta. 1171, pp. 215-218, 1992. Discussed in the spec.
Shin-ichi Tominaga et al.; Biochemical and Biophysical Research Communications 264, pp-14-18, 1999. Discussed in the spec.
Norio Komatsu et al.; Blood, vol. 89, No. 11, pp. 4021-4033, 1997. Discussed in the spec.
Abstract Journal of the $22^{nd}$ annual meeting of the Mol. Biol. Soc. Jpn.
English Summary of JP-A-7-31479, dated Feb. 3, 1995.
Abstract 2P-1005, entitled "Detection and Quantitation of human ST2 protein by using ST2 monoclonal antibodies," in Program and Abstracts of the $22^{nd}$ Annual Meeting of the Molecular Biology Society of Japan (Meeting held Dec. 7-10, 1999). Program and Abstracts published on Nov. 22, 1999. With English translations of title page and Abstract 2P-1005.

(Continued)

*Primary Examiner*—Long V. Le
*Assistant Examiner*—James L. Grun
(74) *Attorney, Agent, or Firm*—Armstrong, Kratz, Quintos, Hanson & Brooks, LLP

(57) ABSTRACT

A method for determining a soluble human ST2 in a sample conveniently at a high sensitivity and an assay kit are provided. By an immunological method comprising a step for bringing a sample into contact with an immobilized antibody formed by binding to an insoluble support a first anti-human ST2 antibody which binds specifically to a non-denatured human ST2, a step for labelling a first reaction product generated in the previous step by reacting said first reaction product with a second anti-human ST2 antibody which binds specifically to a non-denatured human ST2 by recognizing a site different from the site on ST2 where said first anti-human ST2 antibody binds and which is labelled with a label, and a step for determining the amount of the label on said first reaction product which has been labelled, a soluble human ST2 in a sample is determined. In addition, a recombinant ST2 is employed as a standard to prepare a calibration curve, based on which the ST2 in a sample is quantified.

17 Claims, 8 Drawing Sheets

OTHER PUBLICATIONS

English abstract and material from talk "Detection and Quantitation of human ST2 protein by using ST2 monoclonal antibodies," presented at the 22nd Annual Meeting of the Molecular Biology Society of Japan (Meeting held Dec. 7-10, 1999), presented on Dec. 9, 1999.

Abstract 2P-1005, entitled "Detection and Quantitation of human ST2 protein by using ST2 monoclonal antibodies," in Program and Abstracts of the 22nd Annual Meeting of the Molecular Biology Society of Japan (Meeting held Dec. 7-10, 1999). Program and Abstracts published on Nov. 22, 1999. with English translations of title page and Abstract 2P-1005.

English abstract and material from talk "Detection and Quantitation of human St2 protein by using ST2 monoclonal antibodies," presented at the 22nd Annual Metting of the Molecular Biology Society of Japan (Meeting held Dec. 7-10, 1999), presented on Dec. 9, 1999.

Ken Yanagisawa and Shin-ichi Tominaga. "ST2 gene products involve helper T cells", *Clinical Immunology,* 32(5); pp. 513-517, 1999, *English Concise explanation* is attached.

Masakatsu Yamashita and Toshinori Nakayama, "Th1/Th2 cells differentiation", *Clinical Immunology,* 32(5);pp. 532-539, 1999, *English Concise explanation* is attached.

Shin-ichi Tominaga, "ST2 gene, A gene that is induced by growth simulation and encoding a product highly similar to the interleukin 1 receptors", *Journal of Biochemistry,* vol. 67, No. 5, pp. 356-364, 1995, *English Abstract* is attached.

Kinya Nagata and Masataka Nakamura, "Surface molecules distinguishing Th1 and Th2 cells", *Clinical Immunology,* 30(11); pp. 1486-1490, 1998. *English Concise explanation* is attached.

Hideo Nariuchi, "Mechanisms of Th1/Th2 activation and their differentiation", *The Journal of Experimental Medicine,* vol. 17, No. 12, pp. 1420-1424, 1999. *English Abstract* is attached.

Yoichi Kohno, "The Role of T cells in induction of allergic inflammation", *Molecular Medicine,* vol. 34, No. 12, pp. 1436-1446, 1997. *English Concise explanation* is attached.

* cited by examiner

Basic statistic parameter: ST2

|  | Number of cases | Mean | Standard deviation | Standard error |
|---|---|---|---|---|
| atopic asthma | 10 | 3.963 | 3.697 | 1.169 |
| lung cancer | 38 | 0.806 | 0.643 | 0.104 |
| control | 99 | 0.416 | 0.385 | 0.039 |

Fig. 8

MONOCLONAL ANTIBODY AND METHOD AND KIT FOR IMMUNOASSAY OF SOLUBLE HUMAN ST2

CROSS REFERENCE TO RELATED APPLICATIONS

This application is continuation of international application No. PCT/JP00/08723 field Dec. 7, 2000, which claims priority of Japanese application No. 2000-77383 field Mar. 21, 2000.

FIELD OF THE INVENTION

The present invention relates to a monoclonal antibody which binds specifically to a human ST2 which is a protein related to diseases in an immune system. The invention also relates to an immunological method and an assay kit for determining a soluble human ST2 using an anti-human ST2 monoclonal antibody as well as an assay kit.

BACKGROUND OF THE INVENTION

A helper T cell (Th cell) is known as a cell which regulates immune reactions in a body. Via an interaction resulting from the contact between cells or via a release of a substance called cytokine, the helper T cell acts on and regulates a cell which executes an immune reaction.

A helper T cell can be classified, based on the type of the cytokine it produces, broadly into one of the two types, i.e., Th1 and Th2. This concept was proposed in mice for the first time in 1986 by Mosmann et al. They showed that, in a mouse long term-subcultured cell CD4 positive T cell line, a classification is possible into a type I helper T (Th1) cell which produces cytokines such as IL-2, a tumor necrosis factor TNF-β and interferon (IFN)-γ and a type II helper T (Th2) cell which produces cytokines such as IL-4, IL-5, IL-6 and IL-10. This theory was considered to be applicable only to the mouse long term subcultured cell line, and to be difficult to be applied to an in vivo cell. Nevertheless, a subsequent accumulation of findings revealed that the theory can be also applicable to an in-vivo helper T cell.

A further subsequent study revealed that, in many of in-vivo helper T cells, there are populations which can not be classified into any of the subsets proposed by Mosmann. This tendency is remarkable especially in humans rather than in mice, and it was revealed that there are many cells producing cytokines which overlap the both subsets. Then a helper T cell subgroup exhibiting a combination of both patterns was designated as a Th0 cell.

The Th0 cell is considered to be a precursor before differentiation into Th1/Th2. This Th cell subgroup is not homogeneous, and involves a quantitative or qualitative difference in the cytokines produced by each Th0 cell. Accordingly, on the basis of the polarization between the Th1 cell and the Th2 cell, the functions of a Th cell in humans is not considered to be as simple as that in the mouse system. Although the findings in the immune system obtained in the animal experiments such as those in mice have been accumulated, they should carefully be applied to the pathological state of a disease in humans, and a study focusing on a human immune system is required.

A Th1 cell is considered to induce a cellular immunity via the activity of the cytokines it produces (IL-2, TNF-β, IFN-γ). In this context, the cellular immunity is a concept which means an immune reaction undertaken mainly by cells such as cytotoxic T cell (CTL), natural killer (NK) cell and macrophage, which is an immune reaction characterized by an action exerted by these cells directly toward a target. Examples are a phagocytic effect of a macrophage on an invading microorganism, an apoptosis-induced removal of a virus-infected cell by a cytotoxic T cell, a cytotoxic effect of an NK cell on a virus-infected cell, tumor cell or implanted myelocyte. This immune reaction is considered to be involved greatly in an immune reaction toward an intracellular parasite, virus or tumor, in an immune reaction toward a implanted graft, and in an organ-specific autoimmune disease.

IFN-γ which is a cytokine produced by a Th1 cell promotes the differentiation, proliferation, and activation of a cell executing a cellular immunity, whereby directing an in-vivo immune reaction toward the cellular immunity (hereinafter referred to as "type Th1 immune reaction"). A cytokine produced by a Th2 cell described below is known to inhibit a type Th1 immune reaction.

On the contrary to a Th1 cell, a Th2 cell is considered to induce an immune reaction such as a humoral immunity and allergic reaction via the activity of the cytokines it produces (IL-4, IL-5, IL-6, UL-10 and IL-13). The cells involved in these immune reactions are mainly B cells, eosinophiles and mast cells.

In this context, the humoral immunity is a concept which means an immune reaction capable of being transferred to another individual by injecting a serum, which is an immune reaction undertaken mainly by an antibody, i.e., IgG or IgM. The IgG and IgM are involved in a neutralization of a toxin by a cell or in microorganism aggregation or opsonin derivatization, the elimination of which by a macrophage is promoted by its activity.

On the other hand, the secretion of IgE, an antibody which mediates a type I allergic reaction, is promoted by the action of a Th2. The IgE binds to an IgE receptor (Fcε RI) on the surface of a mast cell, and employs as a trigger the crosslinking of an antigen-specific Fcε RI to allow various mediators (histamine, protease, heparin and the like) to be released from the mast cell, whereby inducing an antigen type I allergic reaction.

A cytokine produced by a Th2 cell promotes the humoral immunity or an allergic reaction-involved cell differentiation, proliferation, and activation, whereby directing an in-vivo immune reaction toward such an "antibody-mediated" immune reaction (hereinafter referred to as "type TH2 immune reaction"). A Th1 cell is known to inhibit a type Th2 immune reaction via the cytokines it produces (mainly IFN-γ).

The balance between the Th1 cell and the Th2 cell activation described above or the balance in the cell populations is considered to determine whether an in-vivo immune reaction is type Th1-dominant or type Th2-dominant. It is also recently thought that this balance determines the pathological state of a disease in the immune system.

Such findings are supported by an experiment in which the difference in the genetic background between various experimental mice resulted in a species-related deviation of the immune reaction to type Th1 or Th2 even when the infection origin was identical and the prognosis of the infection also varied.

For example, a C57BL/6 mouse exhibiting a type Th1 immune response to leishmaniasis, which is a type of parasitic infectious diseases, was resistant to the infection, while a Balb/c mouse exhibiting a type Th2 immune response was susceptible to the infection (Heinzel, F. P., Sadick, M. D., Holandy, B. J., et al., Exp. Med. 169:59, 1989). This may be resulting from an advantageous action of the type Th1 immune reaction in preventing the infection in a case of an intracellular infection, which destroys and eliminates a parasite together with a parasitized cell itself.

In addition, the C57BL/6 mouse became susceptible to the infection when treated with IL-4, IL-10 and anti-IFN-γ neutralizing antibody to impart with a type Th2 immune response, while the Balb/c mouse became resistant when treated with IFN-γ, anti-IL-4 neutralizing antibody and anti-IL-10 neutralizing antibody to impart with a type TH1 immune response. Based on such findings, a pathological state was revealed to be affected greatly by the type of the immune response brought by the genetic background of each mouse. Also against an intracellular parasitic pathogen such as those for listeriosis or brucellosis, the prevention of the infection was reported to be effected in a type Th1 immune response (Araya L N, Elzer P H, Rowe G E, Enright F M, Winter A J; J. Immunol. 143:10, 3330–7, 1989).

In an actual immune system, it has been revealed that biophlaxis is performed by controlling the balance between Th1 and Th2 with time.

Extrapolating with these, a control of an in vivo Th1/Th2 balance by the administration of a cytokine or an anti-cytokine antibody is expected to be an effective therapy against an abnormality in the immune system.

While the Th1 and Th2 are grouped by the difference in the cytokines they produces, the difference in the molecule on the surface of each cell (surface marker) has been investigated. If such a difference can be identified, it can serve as a basis for separating each cell to allow an intensive analysis to be performed. Especially if a surface molecule which transmits the signals for differentiation, proliferation or activation specifically to the Th1 or Th2 can be identified, it can directly be a target of the therapy.

However, a surface marker allowing an in-vivo Th1 or Th2 to be distinguished readily has not been established, but there are an increasing number of the reports relating to the surface markers of the Th1 and Th2 in recent years. As a hopeful candidate of the surface marker, a protein molecule expressed specifically on the surface of the Th2 was identified and designated as ST2L (Yanagisawa, K., et al.: FEBS Lett. 318:83, 1993, and Yanagisawa, K., et al.: J. Biochem. 121: 95, 1997).

An ST2L is one of the ST2 gene expression products. The ST2 gene expression products are grouped into the three types discussed below, each of which is considered to be generated by a selective splicing. The first type of the ST2 gene products is a soluble secretion type designated as ST2. This gene was identified earliest among the three types. An ST2 is also referred to as T1, Fit-1 or DER4, and classified into a delayed-early serum reaction gene group in the cell proliferation. Thus, the ST2 is not expressed in a Balb/c-3T3 cell in the G0 phase, but is expressed when a cell is stimulated to proliferate by serum and enters in the phase during the cell cycle of the G1 or S phase subsequent to the G0 phase, and peaked 10 hours after addition of the serum. This protein was identified by us, and we analyzed a gene encoding a human ST2 (see JP-A-6-178687).

The second type is a transmembrane receptor type ST2L. The ST2L has an extremely high homology in the amino acid sequence with an Interleukin-1 (IL-1; a molecule known to be involved in an inflammatory reaction) receptor, with a higher homology being in the intracellular region. Another molecule having a high homology with the IL-1 receptor is an IL-18 receptor, which is a member of a IL-1 receptor family.

It is known that a high affinity receptor is formed by the IL-1 receptor together with a protein AcP or by the IL-18 receptor together with a protein AcPL. Thus, it is suggested that ST2L may form a high affinity receptor together with a protein analogous to the Acp and the like.

Studies on the binding of the ST2L and the IL-1 receptor ligand revealed no binding with any of IL-1α, β receptor antagonist, indicating no clear involvement of IL-1 in a signal transmission pathway.

Studies on a ligand specific to the ST2L include a report of a binding protein purification or cloning, but the cloned protein may just be a binding protein which can not induce any signal, suggesting that a physiological ligand may elsewhere be existed.

In addition, the third type of the ST2 is a variant form of the first type, and designated as ST2V.

We investigated the ST2 expression by performing an RT-PCR using a hematopoietic cultured cell in the previous study. As a result, the ST2 gene was expressed in almost all cells except for lymphocytes.

In lymphocytic series, no expression was found in a cell of the B cell line, while a cell expressing the ST2 gene was found in the T cell line.

For the purpose of a further investigation in the T cell line, we examined the cells for the expression of the ST2 and ST2L in the mouse T cell line using a northern blotting method. As a result, the Th1 cell exhibited no expression of the ST2 even after the simultaneous stimulation with a phorbol ester (PMA) and A23187, while the Th2 cell expressed an mRNA of the ST2L even before any stimulation. After the stimulation, the expression of an mRNA of the ST2 was further induced.

Moreover, we performed an experiment using an EL-4 which is a mouse cultured cell capable of being differentiated into both of the types Th1 and Th2, and found that the EL-4 when stimulated only by PMA produced the type Th1 cytokines such as IL-2 and IFN-γ, while it produced the type Th2 cytokines such as IL-4 and IL-5 when stimulated simultaneously by PMA and dibutyryl cAMP. In this process, no ST2 expression was observed without stimulation, but the expression of the mRNAs of the both of the ST2 and ST2L was induced strongly only when performing a simultaneous stimulation with PMA and dibutyryl cAMP. Based on these findings, the expression of the ST2 exhibits the same behavior as the expression of a type Th2 cytokine in this experimental model.

Also other groups reported that in mice the ST2L protein was expressed constitutively in the Th2 cell unlike to the cytotoxic T cells, and that an analysis using a flow cytometry revealed that the ST2L protein was capable of utilizing as a marker for a Th2 subset (Yanagisawa, K., Naito, Y., Kuroiwa, K. et al., J. Biochem., 121:95, 1997).

Xu et al. found in their study on the ST2 that an antibody against the ST2 induced an in vivo cell death in a Th2 subgroup (Xu D., et al. J.Exp.Med., 787–794: 187, 1998). In this in vivo experiment using the antibody, this antibody was proven to inhibit the susceptibility to the infection with leishmaniasis in Balb/c mice. While the Balb/c strain is susceptible to the infection since it exhibits a type Th2 immune response in leishmaniasis as described above, the type Th1 immune response is considered to be induced by the removal of the Th2 cell by the anti-ST2 antibody. In addition, this antibody exacerbated a collagen-induced arthritis in DBA-1 mice which is considered to be induced in the condition where the type Th1 immune reaction is dominant. These findings indicate that this anti-ST2 antibody inhibited the Th2 whereby inducing the type Th1 immune reaction. Nevertheless, the physiological function of this antibody has not been clarified.

In addition, a reduction in the eosinophile count, in the tissue staining-based Th2 count and in the secretion of the type Th2 cytokines such as IL-4, IL-5, IL-6 and IL-13 in the bronchial washing fluid in a model mouse whose allergic airway inflammation had been induced by administering the anti-ST2 antibody or ST2 was reported (Lohning M. et al.: Proc. Natl. Acad. Sci. USA, 6930–6935: 95, 1998, Xu D. et al.: J. Exp. Med. 787–794: 187, 1998). Based on these reports, it was suggested that an ST2L-mediated signal was inhibited as a result of a competition with a physiological ligand to which the secretion type ST2 might naturally been bound.

The experiments discussed above suggest that the ST2L is associated positively not only with Th1/Th2 balancing but also with Th2 functioning.

The secretion type ST2 is considered to correspond to the extracellular region of the transmembrane type ST2L. As discussed above, both are considered to be generated by a selective splicing.

While it is known that in the Th2 cell the ST2L is expressed constantly but the expression of the ST2 depends on an antigen stimulation, the physiological functions of the ST2 is not known currently. However, as discussed above, since an administration of the ST2 or an administration of a neutralizing antibody against the ST2L inhibits an allergic disease, i.e., a type Th2 immune reaction in a model mouse, a model may be possible in which the secretion type ST2 and the transmembrane type ST2L in blood compete with each other in binding to the physiological ligand and the signal for inducing a type Th2 immune reaction which is transmitted by the ST2L to the inside of a cell is inhibited by the ST2.

Thus, the secretion type ST2 is suggested to be involved in the signal transmission in an immune system and the in-vivo ST2 amount is suggested to serve as a novel index which reflects the condition of the immune system. Nevertheless, no satisfactory biological data have been obtained currently with regard to the secretion type ST2. Moreover, most of the studies on the Th1/Th2 have been conducted in experimental animals such as a mouse, and the resultant data should be applied to humans only after elucidating the functions specific to a human ST2.

For the purpose of accumulating the biological data of the human ST2 and elucidating the in-vivo functions, it is desired to develop a method for measuring the human ST2 in an in-vivo condition, i.e., in a non-denatured state, rapidly and conveniently. As such a method, immunological methods such as an ELISA utilizing a monoclonal antibody against the human ST2 are considered to be effective.

The monoclonal antibody against the human ST2 was attempted to be produced by us, and several types of the anti-human ST2 monoclonal antibodies have been obtained (Yoshida K. et al.,: Hybridoma 419–427:14, 1995). However, such antibodies were obtained using as an immunogen a human ST2 protein obtained by expressing a human ST2 gene in *E.coli*, and bind specifically to a denatured human ST2 but could not recognize a non-denatured human ST2 specifically. Accordingly, they could not be employed for example in an ELISA for measuring a non-denatured human ST2 in a biological sample.

On the other hand, Werenskiold et al. disclosed a method for measuring a human ST2 by means of a PCR method for detecting an mRNA or by means of an immunohistological staining (WO98/430990), but such a method was only qualitative or semi-quantitative, and was not intended to measure the human ST2 quantitatively.

SUMMARY OF THE INVENTION

An objective of the present invention is to provide a monoclonal antibody which binds specifically to a non-denatured human ST2. Another objective of the present invention is to provide a rapid and convenient method for determining a non-denatured soluble (secretion type) human ST2 in a biological sample employing the monoclonal antibody described above. Still another objective of the invention is to provide an effective means for the detection, diagnosis, research, follow-up and prognosis of an abnormality in an immune system such as an allergic disease by the method for determining a soluble human ST2 described above.

We made an effort to accomplish the objectives described above and focused on an immunoassay employing an antibody binding specifically to a human ST2 (hST2), and were successful finally in obtaining a monoclonal antibody which recognizes a non-denatured human ST2, whereby establishing the present invention. Thus, the invention is a monoclonal antibody which binds specifically to a non-denatured human ST2. A non-denatured human ST2 means a human ST2 which is not denatured by a protein degenerating agent such as SDS, for example, a native human ST2 in a human body. A recombinant human ST2 which is prepared using a human ST2cDNA and which is not denatured is also included.

Such a monoclonal antibody includes one binding specifically to a non-denatured soluble (secretion type) human ST2 as well as one binding specifically to a non-denatured membrane-binding human ST2 (human ST2L). Also the monoclonal antibodies produced by the hybridomas designated by the deposition numbers FERM ABP-10190, FERM ABP-10189 and FERM ABP-10191 are included.

The present invention also provides a hybridoma itself which produces a monoclonal antibody described above. Thus, it is a hybridoma producing a monoclonal antibody which binds specifically to a non-denatured human ST2, including the hybridoma designated by the deposition number FERM ABP-10190, the hybridoma designated by the deposition number FERM ABP-10189 and the hybridoma designated by the deposition number FERM ABP-10191.

Furthermore, the invention provides an immunological method for determining a soluble human ST2 in a sample using a monoclonal antibody described above. Such a method includes a method using two types of the monoclonal antibodies, both of which bind specifically to a non-denatured human ST2.

Moreover, the invention provides an immunoassay kit for determining a soluble human ST2 comprising an antibody which binds specifically to a non-denatured human ST2.

BRIEF DESCRIPTION OF THE DRAWINGS

These and other objects and technical advantages of the present invention will be readily apparent from the following description of the preferred exemplary embodiments of the invention in conjunction with the accompanying drawings, in which:

FIG. 8 shows the number of the patients of each disease and normal healthy volunteers participating in the determination in Example 7, together with the means, standard deviations and standard errors.

DETAILED DESCRIPTION OF THE INVENTION

Figure 1:
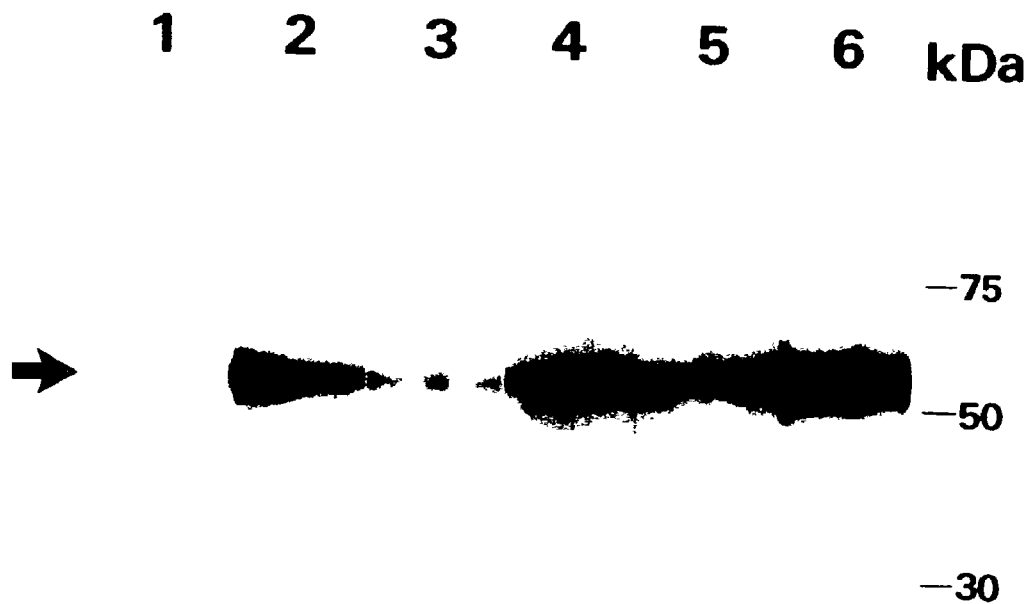
FIG. 1 shows the results of an immunoblotting. Lanes 1 to 3 show the results of the determination of the serum in a mouse immunized with an antigen in Example 1. Lanes 4 to 6 show the results of the determination of the monoclonal antibodies 2A5, FB9 and HB12 in Example 2. The arrow designates the position of an hST2.

A monoclonal antibody of the present invention can be produced as described below. First, an antigen suitable for the preparation of an antibody which binds specifically to a non-denatured human ST2 is prepared, and then is used to immunize an animal such as a mouse. Subsequently, an antibody-producing cell is isolated from the immunized animal, and fused with an myeloma cell, whereby obtaining a hybridoma cell. Then, this hybridoma is monocloned, and then a clone which produces an antibody which has a high specificity to the human ST2 is selected. Finally, the monoclonal antibody produced by the selected clone is examined for its ability of recognizing a non-denatured human ST2.

As an antigen, a human ST2 is employed. The human ST2 can be obtained by purifying a biological sample. It is also possible to use a recombinant human ST2. The recombinant human ST2 can be prepared for example by transducing a human ST2-encoding gene into a eukaryotic cell such as an yeast using a vector followed by the expression in the recombinant cell. Preferably, a mammalian cell such as a COS7 cell is employed as a host cell, in order to obtain a protein whose nature is closer to that of the non-denatured human ST2. Since the nature of a recombinant protein produced by a mammalian cell is considered generally to be closer to a human in-vivo nature when compared with those produced by a yeast and the like, an antibody having high specificity to a human in-vivo non-denatured ST2 can be obtained by using as an antigen a recombinant human ST2 protein obtained using a mammalian cell.

A vector is not limited particularly as long as it can integrate an ST2 gene into a host cell and can allow a gene of interest to be expressed in the host cell, and may be selected appropriately on the basis of the host cell.

It is also possible to use a cell expressing a transmembrane human ST2L on the surface of the cell itself entirely as an antigen. The extracellular region of the human ST2L corresponds to the secretion type human ST2. Accordingly, by using such a cell as an antigen, an antigen whose epitope is the extracellular region of the human ST2L, i.e., the region corresponding to the human ST2, can be obtained. For example, by transfecting a host cell with a vector into which a human ST2L-encoding cDNA has been integrated, a cell capable of expressing the ST2L on its surface can be obtained. It is also possible to obtain a cell which expresses a chimera ST2L molecule on the surface of the cell by transfecting a host cell with a vector into which a gene which encodes the extracellular region of the human ST2L and the transmembrane region and intracellular region of a mouse ST2L has been integrated.

In order to obtain two or more antibodies which recognize different epitopes, it is preferable to perform an immunization using different antigens.

An immunization may be accomplished for example by mixing an antigen described above with a Freund's complete or incomplete adjuvant to form an emulsion and injecting intraperitoneally, subcutaneously or intramuscularly several times at a certain interval for example to a mouse. In addition to a mouse, other animals such as a rat, hamster, rabbit, guinea pig, chicken, sheep and goat may be employed as an animal to be immunized. After establishing the immunity, a spleen is taken out of the immunized animal, from which an antibody-producing cell is obtained. The antibody-producing cell can be also obtained from a lymph node or peripheral blood.

The type of the myeloma cell is not limited particularly, and can be selected appropriately on the basis of the animal to be immunized. Thus, it is preferred to use a myeloma cell derived from an animal of the species similar to that of the antigen-producing cell, and a myeloma cell line PAI can be employed for example when a mouse is employed. The cell fusion can be accomplished for example by mixing the antigen-producing cell and the myeloma cell in a certain ratio followed by adding polyethylene glycol and mixing. It is also possible to effect the cell fusion using an electric pulse.

In order to select a successfully fused hybridoma exclusively, a method employing an ordinary HAT medium (a selection medium containing hypoxanthine, aminopterin and thymidine in a certain ratio) may be used. A hybridoma-containing culture medium is incubated in a vessel such as a 96-well plate for the subsequent selection.

Then, the culture supernatant in each vessel is collected, and a hybridoma which is producing an antibody against a human ST2 is selected for example by an ELISA. The hybridoma in an antibody-positive vessel is cloned by a limiting dilution method, whereby obtaining a monoclonal hybridoma cell line.

An anti-human ST2 monoclonal antibody can be obtained by purifying the culture medium of a hybridoma. It is also possible to allow a hybridoma to proliferate to a level exceeding the intended population, to be implanted intraperitoneally into an animal (for example, mouse) and to proliferate in the ascites, which is then purified. In order to purify the culture medium or ascites mentioned above, an affinity chromatography using protein G and protein A and the like is preferably employed. It is also possible to use an affinity chromatography on an immobilized antigen. Also an ion exchange chromatography, gel filtration chromatography, sodium sulfate fractionation and centrifugation can be employed, each of which are employed alone or in combination with each other.

An anti-human ST2 monoclonal antibody thus obtained can be examined for its ability of recognizing a non-denatured human ST2 specifically for example by a cell ELISA employing a cell on whose surface the human ST2L is expressed. In such a method, the human ST2L expressed on the surface of the cell is not denatured since the cell is employed without being immobilized. The cell ELISA employing such a cell allows the reactivity between the non-denatured human ST2 and each monoclonal antibody to be verified since the extracellular region of the human ST2L corresponds to the human ST2 as described above.

A hybridoma producing an anti-human ST2 monoclonal antibody which binds specifically to a non-denatured human ST2 may for example be those designated by the deposition numbers FERM ABP-10190, FERM ABP-10189 and FERM ABP-10191, which have been deposited to the following international deposition organization.

Name: National Institute of Bioscience and Human-Technology, Agency of Industrial Science and Technology of the Ministry of International Trade and Industry.

Address: 1–3, HIGASHI 1-chome, TSUKUBA City, IBARAKI Pref., JAPAN (305-0046).

Date of deposition: Mar. 15, 2000.

By using a monoclonal antibody prepared by a method described above, a soluble human ST2 can be determined immunologically. The determination may employ a qualitative or quantitative method such as an ELISA, radioimmunoassay, FACS, immunoprecipitation, immunoblotting and the like. A preferred determination may be conducted for example as follows. Thus, an immunological method for determining a soluble human ST2 comprising a) a step for bringing an insoluble support to a first anti-human ST2 antibody which binds specifically to a non-denatured human ST2, b) a step for labeling a first reaction product generated in step a) described above by reacting said first reaction product with a second anti-human ST2 antibody which binds specifically to a non-denatured human ST2 by recognizing a site different from the site on ST2 where said first anti-human ST2 antibody binds and which is labeled with a label and c) a step for determining the amount of the label on said first reaction product which has been labeled can be employed.

The determination method described above may further comprise the following steps: d) a step for reacting said immobilized antibody with a soluble human ST2 as a standard, e) a step for labeling a second reaction product generated in step d) described above by reacting said second reaction product with a second anti-human ST2 antibody which has been labeled with said label, f) a step for preparing a calibration curve by determining the amount of the label on said second reaction product and g) a step for quantifying the soluble human ST2 in said sample based on the amount of the label on said first reaction product and said calibration curve. In these steps d) to g), a calibration curve can be obtained using a soluble human ST2 as a standard. Then, on the basis of this calibration curve, the label on the first reaction product is quantified, whereby quantifying the soluble ST2 in the sample.

In the method described above, a monoclonal antibody which binds specifically to a non-denatured human ST2 prepared by the method described above is employed preferably as the first anti-human ST2 antibody or the second anti-human ST2 antibody. Depending on the degree of the specificity of the monoclonal antibody, a highly sensitive determination can be accomplished. It is also possible to use a combination of several types of the monoclonal antibodies as the first anti-human ST2 antibody or the second anti-human ST2 antibody. Preferably, a monoclonal antibody produced by one or more hybridomas selected from the group of the hybridomas designated by the deposition numbers FERM ABP-10190, FERM ABP-10189 and FERM P-10191 is employed.

It is also preferable to use two types of anti-human ST2 monoclonal antibodies recognizing different epitopes which are produced by the method described above as the first anti-human ST2 antibody and the second anti-human ST2 antibody. By using a combination of two or more highly specific monoclonal antibodies, more sensitive determination becomes possible.

Each anti-human ST2 monoclonal antibody can be examined for its epitope by a competitive ELISA using the human ST2. Thus, two types of anti-human ST2 monoclonal antibodies are reacted simultaneously with a human ST2 to observe the competition between the both. As a result, two types of the anti-human ST2 monoclonal antibodies which are non-competitive can be selected as a combination of the monoclonal antibodies whose epitopes are different from each other.

It is possible to use as a first anti-human ST2 antibody a monoclonal antibody produced by one or two hybridomas selected from the group of the hybridomas designated by the deposition numbers FERM ABP-10190, FERM ABP-10189 and FERM ABP-10191, and as a second anti-human ST2 antibody a monoclonal antibody produced by one or two hybridomas which are not selected in said group. More preferably, a first anti-human ST2 antibody is a monoclonal antibody produced by the hybridomas designated by the deposition number FERM ABP-10190 or FERM ABP-10191, and a second anti-human ST2 antibody is a monoclonal antibody produced by the hybridoma designated by the deposition number FERM ABP-10189.

It is also possible that a first anti-human ST2 antibody and/or a second anti-human ST2 antibody are polyclonal antibodies.

It is preferable to use a recombinant human ST2 (hereinafter referred to as rhST2) as a soluble human ST2 which serves as said standard. An rhST2 is preferable since it can be produced homogeneously at a large scale. Such an rhST2 may for example be those expressed as a fusion protein of a human ST2 with GST, β-galactosidase, maltose-binding protein or histidine (His) tag and the like. These fusion proteins can readily be purified by an ordinary method.

An insoluble support employed in an immobilized antibody may for example be a water-insoluble substance such as a resin including a polystyrene resin, polycarbonate resin, silicone resin, nylon resin and the like as well as a glass, the nature of the material of which is not limited particularly. The immobilization of a first anti-ST2 antibody to this insoluble support is accomplished by a physical adsorption or chemical adsorption.

A label may be selected from the group consisting of a peroxidase, β-D-galactosidase, microperoxidase, horse radish peroxidase (HRP), fluorescein isothiocyanate (FITC), rhodamine isothiocyanate (RITC), alkaline phosphatase, biotin and radioactive substances. A higher sensitivity in the determination can be achieved especially by a reaction with avidin peroxidase using biotin as a label.

A sample may for example be a body fluid such as a serum, plasma, urine, cerebrospinal fluid, ascites, pleural effusion and the like. Preferably, a serum is employed. A serum allows a determination to be conducted conveniently.

An immunoassay kit for determining a soluble human ST2 can be constructed using a monoclonal antibody which binds specifically to a non-denatured human ST2 obtained by a method described above. Preferably, a kit is constructed by using one or more monoclonal antibodies produced by one or more hybridomas selected from the group of the hybridomas designated by the deposition numbers FERM ABP-10190, FERM ABP-10189 and FERM ABP-10191.

A kit may further contain the following components. Thus, a first anti-human ST2 antibody which binds specifically to a non-denatured human ST2, a second anti-human ST2 antibody which binds specifically to the non-denatured human ST2 by recognizing a site different from the site where said first anti-human ST2 antibody binds and which is labeled with a label and a soluble human ST2 antibody as a standard may be contained. In such a case, an immobilized antibody to an insoluble support may be employed.

A monoclonal antibody which binds specifically to a non-denatured human ST2 prepared by the method described above is employed preferably as the first anti-human ST2 antibody or the second anti-human ST2 antibody. Depending on the degree of the specificity of the monoclonal antibody, a highly sensitive determination can be accomplished. It is also possible to use a combination of several types of the monoclonal antibodies as the first anti-human ST2 antibody or the second anti-human ST2 antibody. Preferably, a monoclonal antibody produced by one or more hybridomas selected from the group of the hybridomas designated by the deposition numbers FERM ABP-10190, FERM ABP-10189 and FERM ABP-10191 is employed. It is also possible to use a combination of several types of the monoclonal antibodies as the first anti-human ST2 antibody or the second anti-human ST2 antibody.

It is also preferable to use two types of anti-human ST2 monoclonal antibodies recognizing different epitopes which are produced by the method described above as the first anti-human ST2 antibody and the second anti-human ST2 antibody. By using a combination of two highly specific monoclonal antibodies, more sensitive determination becomes possible. In such a case, it is preferable to use as a first anti-human ST2 antibody a monoclonal antibody produced by one or two hybridomas selected from the group of the hybridomas designated by the deposition numbers FERM ABP-10190, FERM ABP-10189 and FERM ABP-10191 and as a second anti-human ST2 antibody a monoclonal antibody produced by one or two hybridomas which are not selected in said group. More preferably, a first anti-human ST2 antibody can be a monoclonal antibody produced by the hybridomas designated by the deposition number FERM ABP-10190 or FERM ABP-10191, and a second anti-human ST2 antibody can be a monoclonal antibody produced by the hybridoma designated by the deposition number FERM ABP-10189.

It is also possible that a first anti-human ST2 antibody and/or a second anti-human ST2 antibody are polyclonal antibodies.

It is preferable to use an rhST2 as a soluble human ST2 which serves as said standard. An rhST2 is preferable since it can be produced homogeneously at a large scale. Such a rhST2 may for example be those expressed as a fusion protein of a human ST2 with GST, β-galactosidase, maltose-binding protein or histidine (His) tag and the like. These fusion proteins can readily be purified by an ordinary method.

An insoluble support employed in an immobilized antibody may for example be a water-insoluble substance such as a resin including a polystyrene resin, polycarbonate resin, silicone resin, nylon resin and the like as well as a glass, the nature of the material of which is not limited particularly. The immobilization of a first anti-ST2 antibody to this insoluble support is accomplished by a physical adsorption or chemical adsorption.

A label may be selected from the group consisting of a peroxidase, β-D-galactosidase, microperoxidase, horse radish peroxidase (HRP), fluorescein isothiocyanate (FITC), rhodamine isothiocyanate (RITC), alkaline phosphatase, biotin and radioactive substances. A higher sensitivity in the determination can be achieved especially by a reaction with avidin peroxidase using biotin as a label.

Using a monoclonal antibody described above, a membrane-binding human ST2L expressed on the surface of a cell can be determined immunologically. The determination may be effected by extracting a human ST2L from a cell which is expressing the human ST2L and purifying prior to the determination, or by a direct measurement of the human ST2L expressed on the surface of an viable cell. As a latter method, a cell ELISA may be exemplified. The human ST2L can be also measured by an ELISA, radioimmunoassay, FACS, immunoprecipitation, immunoblotting and the like.

By measuring a human ST2L, the ratio between the Th1 cell and the Th2 cell in a sample can for example be determined. As a result, a means useful for diagnosing a disease associated with the balance between the both cells may be provided. A means useful for elucidating the mechanism in an immune system may also be provided.

EXAMPLE 1

Preparation of Monoclonal Antibody Binding Specifically to Non-denatured Human ST2

(1-1) Preparation of Antigen

Two different antibodies were employed to obtain a monoclonal antibody binding specifically to a non-denatured human ST2 (hereinafter referred to as hST2). The first antigen employed was a soluble recombinant hST2 which was produced and secreted in a COS7 cell into which an hST2 gene had been transduced. The second antigen employed was a COS7 cell expressing a chimera molecule HMS whose extracellular region corresponded to a human ST2L (hereinafter referred to as hST2L) and whose transmembrane region and intracellular region corresponded to a mouse ST2L. The method for preparing each antigen is described below.

a. Preparation of Soluble Recombinant hST2 (rhST2)

An expression vector containing all coding region of a human whole length ST2 cDNA (Sequence ID No.1) (pEF-BOS-ST2H) was constructed and transfected into a COS7 cell (see Tominaga S., et al.,: Biochim. Biophys. Acta. 215–218:1171, 1992 and Yoshida K., et al.,: Hybridoma, 419–427: 14, 1995). Subsequently, the rhST2 was purified from the culture supernatant of the transfected COS7 cell using a heparin agarose column and MonoQ HR5/5 column (Amersham Pharmacia Biotech) (See Yanagisawa K., et al., J. Biochem. 95–103: 121, 1997). The final purification product of the rhST2 exhibited a single band in an SDS-PAGE silver staining. The concentration of this protein was determined by a Bradford method using BSA as a standard.

b. Preparation of COS7 Cell Expressing Chimera Molecule HMS

As another antigen, a COS7 cell expressing a chimera molecule HMS whose extracellular region corresponded to a hST2L and whose transmembrane region and intracellular region corresponded to a mouse ST2L was prepared by the method described below. Thus, a pEF-BOS-HMS producing an HMS chimera molecule containing the extracellular region of the human ST2L and the transmembrane region and the intracellular region of a mouse ST2L was transduced into a COS7 cell. The HMS chimera molecule and the pEF-BOS-HMS were produced according to the method by Yoshida et al. (See, Yoshida K., et al.: Hybridoma, 419–427: 14, 1995). For introducing the pEF-BOS-HMS into the COS7 cell, the COS7 cell was washed first with an isotonic tris buffer, 20 mM Tris-HCl (pH7.5 at 20° C.), 120 mM NaCl and combined with the pEF-BOS-HMS mixed with a DEAR-dextran solution, and then incubated at room temperature for 15 minutes. After washing with the isotonic tris buffer, the transfected COS7 cell was treated with an isotonic tris buffer containing 20% (w/v) glycerol at room temperature for 2 minutes. Subsequently, the cell was treated with a DME+10% FBS containing 150 μM chloroquine for 3 hours under the atmosphere of 5% $CO_2$ and 37° C. After the treatments described above, the culture medium was exchanged to a DME+10% FBS, which was incubated in the presence of 5% $CO_2$ at 37° C. After incubating for 48 hours, the cell was suspended in a PBS, which was used as an antigen solution used in the immunization described below.

(1-2) Preparation of Antibody-Producing Cell a. Preparation of Antibody-producing Cell Using rhST2 as Antigen 50 μg of the rhST2 prepared as described above was mixed with a Freund complete adjuvant to form an emulsion, which was injected subcutaneously to a Balb/c mouse (6-week old, female). In a second immunization, 25 μg of the rhST2 was mixed with a Freund incomplete adjuvant and injected subcutaneously in the 2nd week in a manner similar to that described above. In an additional immunization, 25 μg of the rhST2 mixed with a Freund incomplete adjuvant was injected intraperitoneally to the mouse. 5 Days after the final immunization, the spleen cell of the mouse was isolated. The isolated spleen cell was ground in a serum-free RPMI-1640 medium over a stainless steel mesh, and the spleen cell suspension was centrifuged (1500 rpm, 7 minutes). The centrifugation pellet was collected and suspended in the serum-free RPMI-1640 medium. The cell was washed further twice with the serum-free RPMI-1640 medium to obtain an antibody-producing mouse spleen cell.

In order to verify the establishment of the immunity, the mouse serum was collected and subjected to an immunoblotting. The immunoblotting was effected similarly to the method in (2-1) described below. The results are shown in Lane 2 in FIG. 1. Lane 1 is a control using the serum of the mouse before immunization as a sample. In Lane 2, a band was observed in the position of the rhST2 protein designated by the arrow, proving that the antibody to recognize the rhST2 was produced.

b. Preparation of Antibody-Producing Cell Using COS7 Cell Expressing Chimera Molecule HMS as Antigen First, a Balb/c mouse (6-week old, female) was treated only with 100 μl of the Freund complete adjuvant via a subcutaneous injection. After 24 hours, 200 μl of the COS7 antigen (containing $1 \times 10^6$ cells of COS7 cell) prepared by the method described above was inoculated at the same site of the subcutaneous injection described above. In an additional immunization, 100 μl of the COS7 antigen (containing $5 \times 10^5$ cells of COS7 cell) was inoculated similarly after 24 hours. 5 days after the final immunization, the spleen cell of the mouse was isolated. The isolated spleen cell was ground in a serum-free RPMI-1640 medium over a stainless steel mesh, and the spleen cell suspension was centrifuged (1500 rpm, 7 minutes). The centrifugation pellet was collected and suspended in the serum-free RPMI-1640 medium. The cell was washed further twice with the serum-free RPMI-1640 medium to obtain an antibody-producing mouse spleen cell.

In order to verify the establishment of the immunity, the mouse serum was collected and subjected to an immunoblotting. The immunoblotting was effected similarly to the method in (2-1) described below. The results are shown in Lane 3 in FIG. 1. As described above, Lane 1 is a control using the serum of the mouse before immunization as a sample. In Lane 3, a band was observed in the position of the rhST2 protein designated by the arrow, proving that the antibody to recognize the rhST2 was also produced when using the chimera molecule HMS-expressing COS7 cell as an antigen.

(1-3) Preparation of Mouse Myeloma Cell

As a mouse myeloma cell, a cell line PAI was employed. The mouse myeloma cell was incubated in a FCS-supplemented RPMI 1640 complete medium (*WITTAKER* BIOPRODUCTS) containing L-glutamine (1 mM, Flow Laboratories), β-mercaptoethanol ($5 \times 10^{-6}$, Gibco), N-2-hydroxyethylpiperazine-N'-2-ethanesulfonic acid (Hepes) (pH7.2)(10 mM, Gibco), non-essential amino acid (0.1 mM, Gibco) and sodium pyruvate (1 mM, Gibco).

(1-4) Preparation of Hybridoma and Cloning

A mixture of the antibody-producing mouse spleen cell prepared as described in Section a or Section b in (1-2) described above and the mouse myeloma cell in (1-3) was combined with polyethylene glycol 4000 (50% (w/v) in RPMI1640) (Merck) and stirred to effect a fusion reaction. The mixture was dispensed into a 96-well plate and incubated in a HAT selection medium (hybridoma incubation plate).

An anti-hST2 antibody-producing hybridoma was selected by a microplate enzyme-linked immunosorbent assay (ELISA, enzymatic immunoassay) using an hST2-supporting plate. The hST2-supporting plate was prepared as described below. First, a 96-well plate was provided and 50 μl of a 2 μg/ml solution of the human ST2 in a sodium carbonate buffer (pH 9.0) was added to each well. The hST2 was allowed to adsorb on the bottom of each well by allowing it to stand at 4° C. overnight. After removing the solution in each well, 200 μl of a PBS+0.1% (w/v)BSA was added to each well and allowed to stand for 1 hour or longer in order to prevent any non-specific binding. Subsequently, each well was washed three times with 100 μl of a PBS. To each well of the hST2-supporting plate thus prepared, 50 μl of the culture supernatant of each well of the hybridoma culture plate described above was added, and allowed to react for 1 hour. After washing three times with the PBS, a solution of horse radish peroxidase (HRP)-binding goat anti-mouse IgG antibody (Bio-Rad) was added and allowed to react for 30 minutes. After washing 4 times with the PBS, 100 μl of a 10 mM o-phenylenediamine (OPD)-0.01% $H_2O_2$ dissolved in a 50 mM sodium acetate buffer (pH 5.0) was added to each well, and allowed to react for 20 minutes. After the reactions described above, 2N sulfuric acid was added to quench the reaction, and the absorbance of each well at 492 nm was measured using a microplate reader (NIPPON INTERMED). All procedure was conducted at room temperature.

As a result of the screening described above, 20 wells were revealed to be positive. Among these 20 wells, 3 wells exhibiting the highest reactivity were selected using a cell ELISA, western blotting and flow cytometry, and the hybridoma in each well was cloned by a limiting dilution method. As a result, three hybridoma clones (2A5: deposition number FERM ABP-10189, FB9: deposition number FERM ABP-10190 and HB12: deposition number FERM ABP-10191). Each hybridoma clone was deposited to the international organization shown below.

International Deposition Organization:

Name: National Institute of Bioscience and Human-Technology, Agency of Industrial Science and Technology of the Ministry of International Trade and Industry.

Address: 1–3, HIGASHI 1-chome, TSUKUBA City, IBARAKI Pref., JAPAN (305-0046).
Date of deposition: Mar. 15, 2000.
Deposition number: FERM ABP-10190 (FB9), FERM ABP-10189 (2A5), FERM ABP-10191 (HB12).

Hybridoma clones 2A5 and FB9 were the clones obtained using the rhST2 in Section a in (1-1) described above as an antigen, while the hybridoma clone HB12 was the clone obtained using the chimera molecule HMS-expressing COS7 cell in Section b in (1-1) described above.

Each hybridoma thus cloned was proliferated to $10^6$ cells or more in a 25-cm$^2$ culture flask. For the purpose of obtaining an ascites, each hybridoma recovered from the flask was inoculated intraperitoneally to a Balb/c mouse (female, 8 to 10-week old).

The antibody produced by each hybridoma was characterized using the ascites.

(1-5) Purification and Labelling of Monoclonal Antibody

The ascites obtained from each hybridoma described above was purified by an affinity column chromatography on a Hi-Trap protein G column (Amersham Pharmacia Biotech) to obtain monoclonal antibodies 2A5, FB9 and HB12.

Each monoclonal antibody was labeled by binding to biotin, horse radish peroxidase (HRP) or fluorescein isothiocyanate (FITC). Biotin was bound using an ECL protein biotinylation module (Amersham Pharmacia Biotech). The labeling with the HRP was conducted using a peroxidase labeling kit (Boehringer Mannheim) according to the instruction by the manufacturer. The labeling with FITC was conducted by dissolving each monoclonal antibody at 2 mg/ml in a 0.1M sodium carbonate buffer (pH 9.0), adding 15 µg/ml of FITC (DOJINSHA) and then reacting overnight at 4° C. while being protected from light. The reaction was quenched by adding a 1/10 volume of 1.5 M hydroxylamine hydrochloride (pH 8.0) and allowing to stand for 30 minutes. In order to remove any non-binding FITC, the reaction solution was subjected to ultrafiltration using an Ultrafree C3 (Millipore).

EXAMPLE 2

Examination of Monoclonal Antibody Activity a. Immunoblotting Method

In order to examine the monoclonal antibodies 2A5, FB9 and HB12 obtained as described above for their activities on the hST2, an immunoblotting method was employed.

First, the rhST2 purified partially on a heparin agarose column in Section a in (1-1) described above was developed by a 10% SDS-PAGE and then transferred onto a PVDF membrane filter. Subsequently, the filter was cut into strips, and each filter was blocked with 10 mg/ml skim milk dissolved in a 0.05% (v/v) solution of Tween 20 in a tris buffered physiological saline (T-TBS; pH 7.5). Then each filter was reacted with the purified monoclonal antibody obtained in (1-5) described above dissolved in a skin milk/T-TBS. After reacting for 1 hour, the filter was washed three times with the skim milk/T-TBS, and reacted with an HRP-binding goat anti-mouse IgG dissolved in the skim milk/T-TBS for 30 minutes. After washing three times, the bands of the protein were detected by a chemiluminscence method using an ECL system (Amersham Pharmacia Biotech). All reactions and measurements were conducted at room temperature.

The results of the detection are shown in FIG. 1. Lane 4, Lane 5 and Lane 6 represent the samples treated with purified monoclonal antibodies 2A5, FB9 and HB12, respectively. Each sample exhibited a marked band at the position of the rhST2 protein designated by the arrow, indicating that each antibody had a high reactivity with the hST2.

b. Immunoprecipitation Method

In order to examine whether monoclonal antibodies 2A5, FB9 and HB12 were capable of detecting an in vivo hST2L, an immunoprecipitation assay was conducted.

First, about $2\times10^7$ cells of the COS7 cell were transfected with a pEF-BOS plasmid obtained by integrating the hST2LcDNA (Sequence ID No.2) into an expression vector pEF-BOS. Subsequently, the transfected COS7 cell was subjected to lysis, and extracted with 1 ml of a TNE buffer, 10 mM Tris-HCl (pH 7.8), 1 mM EDTA, 0.15 M NaCl, 1% (w/v) Nonidet P-40. The extract thus obtained was combined with 15 µl of a 50% (v/v) suspension (in the TNE buffer) of a protein A-binding Sepharose 4B (Amersham Pharmacia Biotech), and allowed to stand at 4° C. for 2 hours. The supernatant obtained by centrifugation was combined with each of monoclonal antibodies 2A5, FB9 and HB12, and each tube was stirred rotatively at 4° C. for 2 hours. Subsequently, 20 µl of a 50% (v/v) suspension (in the TNE buffer) of the protein A-binding Sepharose 4B was added to each tube, and stirred rotatively at 4° C. for 2 hours. After centrifugation, the pellet was washed five times with the TNE buffer. The pellet was suspended in 50 µl of an SDS sample buffer whose concentration was higher by twice, and treated at 95° C. for 10 minutes, and then centrifuged.

The supernatant thus obtained (20 µl) by a treatment above was developed by the SDS-PAGE. Thereafter, the analysis was performed by an immunoblotting employing a G7 monoclonal antibody capable of recognizing the hST2 (Yoshida K., et al.,: Hybridoma 419–427:14, 1995) and an anti-mouse IgM-HRP conjugate. The results are shown in FIG. 2.

Figure 2:
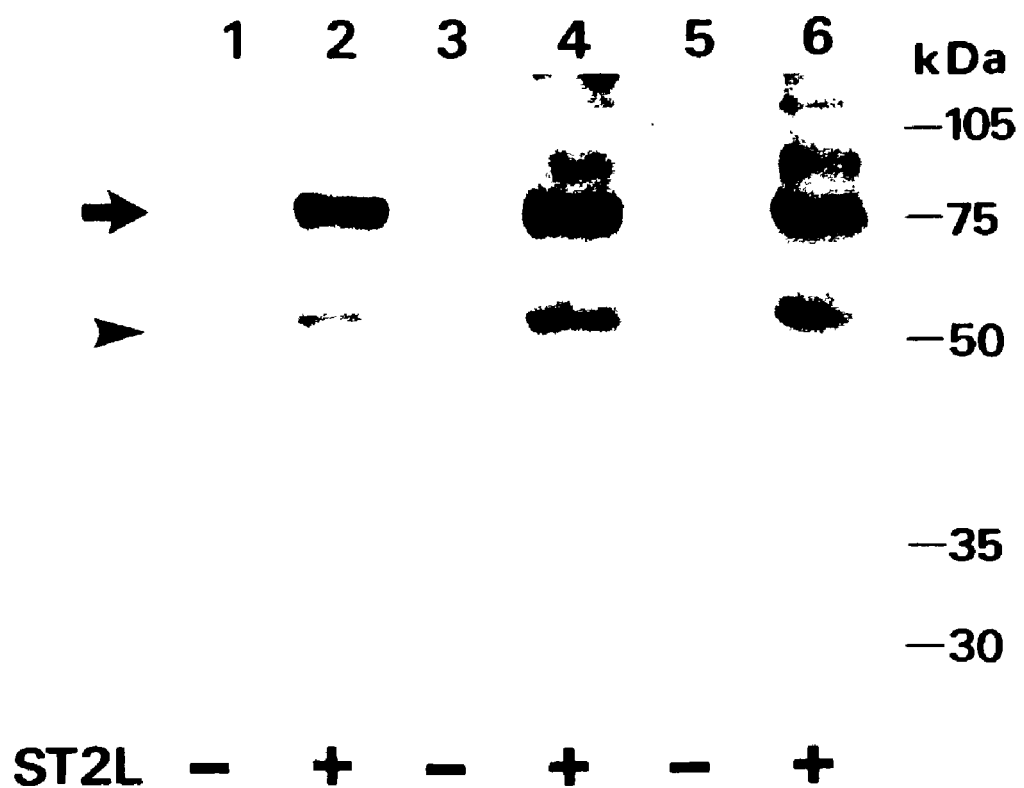
FIG. 2 shows the results of the immunoprecipitation assay in Example 2. The arrow and the arrowhead represent the positions of the hST2L of about 80 kDa including an added saccharide chain and the hST2L of about 60 kDa including no added saccharide chain, respectively.

In FIG. 2, Lanes 2, 4 and 6 represent the results of the immunoprecipitation by monoclonal antibodies 2A5 (Lane 2), FB9 (Lane 4) and HB12 (Lane 6), respectively, using the COS7 cell transfected with the hST2LcDNA-containing pEF-BOS as described above. Lanes 1, 3 and 5 are the controls of the samples to Lanes 2, 4 and 6, respectively, and represent the results of the procedure similar to those described above using a pEF-BOS blank vector instead of the hST2LcDNA-containing pEF-BOS. The arrow and the arrowhead represent the positions of the hST2L of about 80 kDa which had a saccharide chain (i.e., to which a saccharide chain was added) and the hST2L of about 60 kDa which had no saccharide chain (i.e., to which no saccharide chain was added), respectively. As shown in this figure, all monoclonal antibodies allowed every hST2L to be immunoprecipitated. Based on the results described above, each of monoclonal antibodies 2A5, FB9 and HB12 was proven to be capable of recognizing specifically a product by the transfected hST2LcDNA. It was also revealed that the reactivity with each antibody did not depend qualitatively on the presence or absence of the saccharide chain in the ST2L.

EXAMPLE 3

Reactivity of Monoclonal Antibody with Non-denatured hST2 and Epitope (3-1) Cell ELISA Method It was examined whether monoclonal antibodies 2A5, FB9 and HB12 were capable of recognizing a non-denatured hST2 or not by a cell ELISA employing a viable cell which was expressing the hST2L on its cell surface.

A COS7 cell was transfected with a pEF-BOS plasmid obtained by integrating the hST2LcDNA into the expression vector pEF-BOS, and the transfected cell was incubated in a 96-well plate for 48 hours. Subsequently, each well was made free of the culture medium, and charged with each monoclonal antibody labeled with the HRP, together with a varying concentration of the rhST2. Thereafter, the plate was incubated in the presence of 5% $CO_2$ at 37° C. for 15 minutes. After these reactions, the cell in each well was washed three times with a PBS gently, and the HRP enzymatic activity in each well was assayed.

Figure 3:
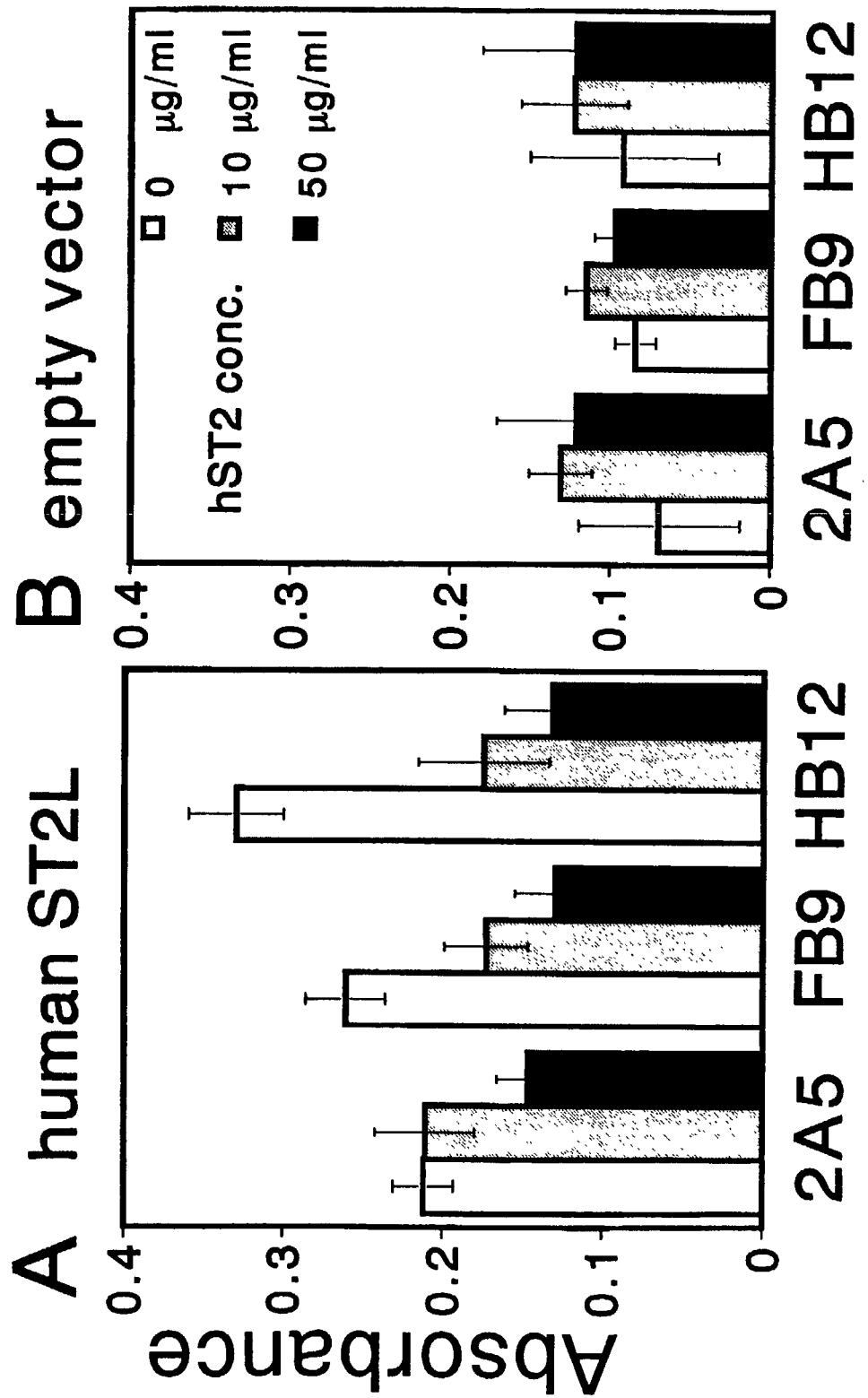
FIGS. 3A and 3B show the graph indicating the results of the cell ELISA in Example 3.

The graph of results of the assay are shown in FIG. 3. In the figure graph A shows the results of the sample obtained by the procedure described above. Graph B shows the results of the sample subjected to the similar procedure using a blank pEF-BOS plasmid containing no hST2LcDNA instead of the pEF-BOS plasmid containing the hST2LcDNA. White, gray and black bars represent the results of the reaction with the monoclonal antibody in the presence of 0 µg/ml, 10 µg/ml and 50 µg/ml of the rhST2 respectively. Each data is represented as a mean ± standard deviation (SD: n=8).

As shown in FIG. 3A, the interaction between the COS7 cell and the HRP-labelled antibody was reduced in the presence of the rhST2. Accordingly, the interaction was proven to be specific. In addition, since the cell was not immobilized in this experiment, the hST2L protein expressed on the surface of the transfected COS7 cell had not been denatured, and was in a native condition. Accordingly, this experiment revealed that each monoclonal antibody was capable of recognizing the non-denatured hST2L expressed on the viable cell surface. Since the extracellular region of the hST2L corresponds to the hST2, each monoclonal antibody was proven to be capable of recognizing a non-denatured hST2.

(3-2) Competitive ELISA Method

In order to examine whether monoclonal antibodies 2A5, FB9 and HB12 recognize the same site on the hST2, a competitive ELISA method was performed as described below.

First, biotinylated monoclonal antibodies 2A5, FB9 and HB12 (each 200 ng/ml) were added to hST2 protein-coated 96-well plates, together with non-labeled monoclonal antibodies 2A5, FB9 and HB12 at various concentrations, and then reacted at room temperature for 1 hour. Each plate was washed three times, charged with a streptoavidin-HRP conjugate, and then reacted further for 30 minutes. After washing the plate, the peroxidase activity in each plate was assayed. The results are shown as graphs in FIG. 4. The data represented are the means of 4 independent experiments.

Figure 4:
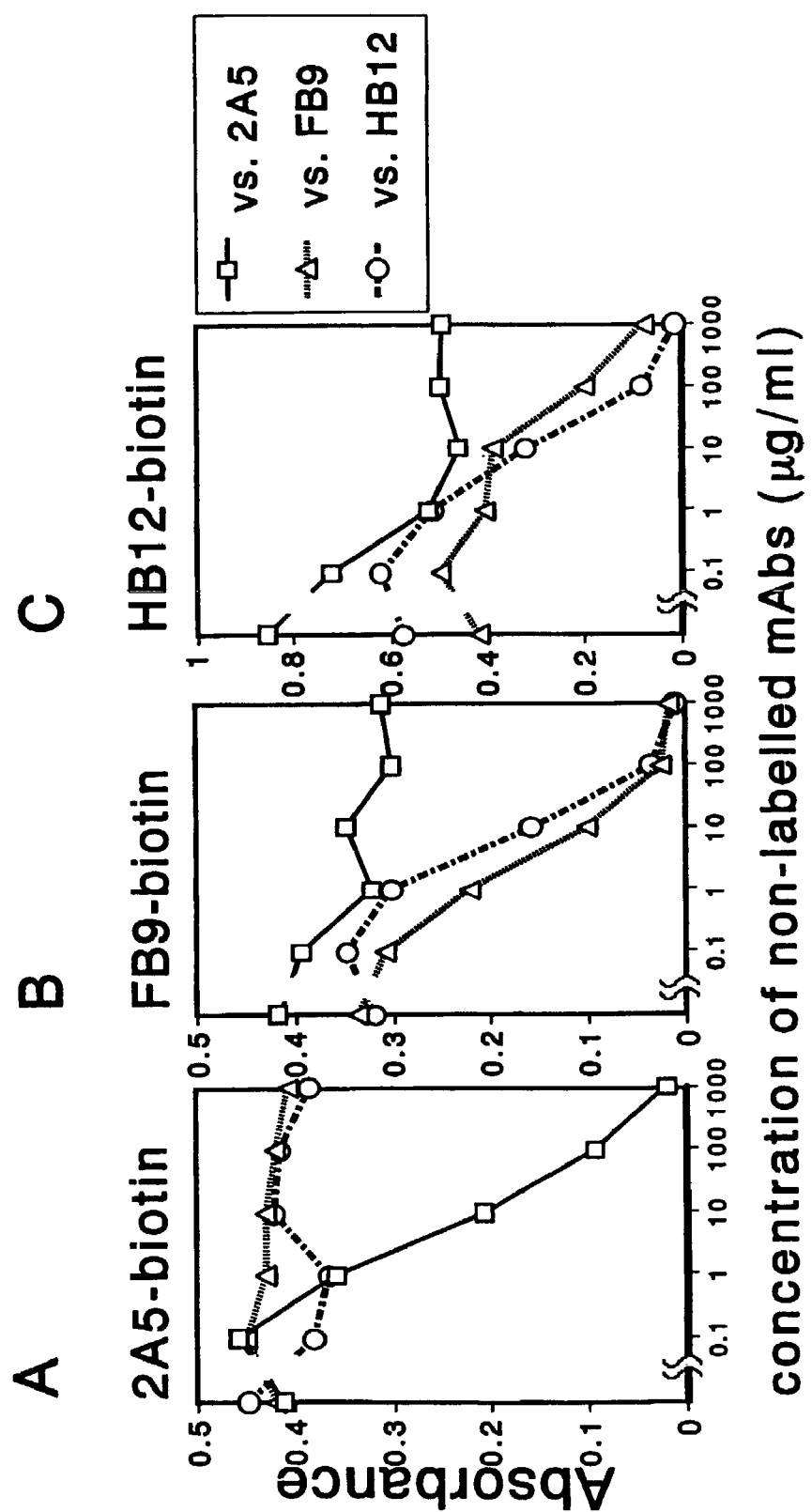
FIGS. 4A, 4B and 4C show the graph indicating the results of the competitive ELISA in Example 3.

As shown in FIG. 4, the binding of monoclonal antibody 2A5 was inhibited competitively only by itself (panel A). Thus, the monoclonal antibody 2A5 was proven to bond to the hST2 by recognizing the site different from those recognized by other monoclonal antibodies. On the other hand, based on panels B and C, the monoclonal antibody FB9 and the monoclonal antibody HB12 inhibited each other from binding to the hST2 in a dose-dependent manner. Thus, the monoclonal antibody FB9 and the monoclonal antibody HB12 were proven to bind to the hST2 competitively with each other.

Based on the results described above, the site on the hST2 recognized by the monoclonal antibody FB9 and the monoclonal antibody HB12 was proven to be different from the site on the hST2 recognized by the monoclonal antibody 2A5.

EXAMPLE 4

Verification of Monoclonal Antibody Reactivity

In (3-1) described above, monoclonal antibodies 2A5, FB9 and HB12 were revealed to recognize the hST2L in a viable COS7 cell. Accordingly, each monoclonal antibody was examined for the possibility of being subjected to a flow cytometry.

First, a COS7 cell was transfected with a pEF-BOS plasmid containing the hST2LcDNA in order to express the hST21 on the surface of the cell. The transfect COS7 cell was peeled from the culture dish in the absence of trypsin, and then suspended in a PBS. Then each of monoclonal antibodies 2A5, FB9 and HB12 was added, and reacted at room temperature for 15 minutes. After washing three times with the PBS, a rabbit anti-mouse Ig-FITC label (DAKO) was added as a secondary antibody, and treated at room temperature for 15 minutes, and then washed three times again with the PBS. Thereafter, the cell was suspended in a PBS containing 2 µg/ml of propidium iodide, and analyzed by flow cytometry using FACScan (Becton-Dickinson). As a control, a sample obtained by transfecting a COS7 cell with a blank pEF-BOS plasmid instead of the pEF-BOS plasmid containing the ST2LcDNA was employed. The results of each sample are shown in A in FIG. 5.

Figure 5:
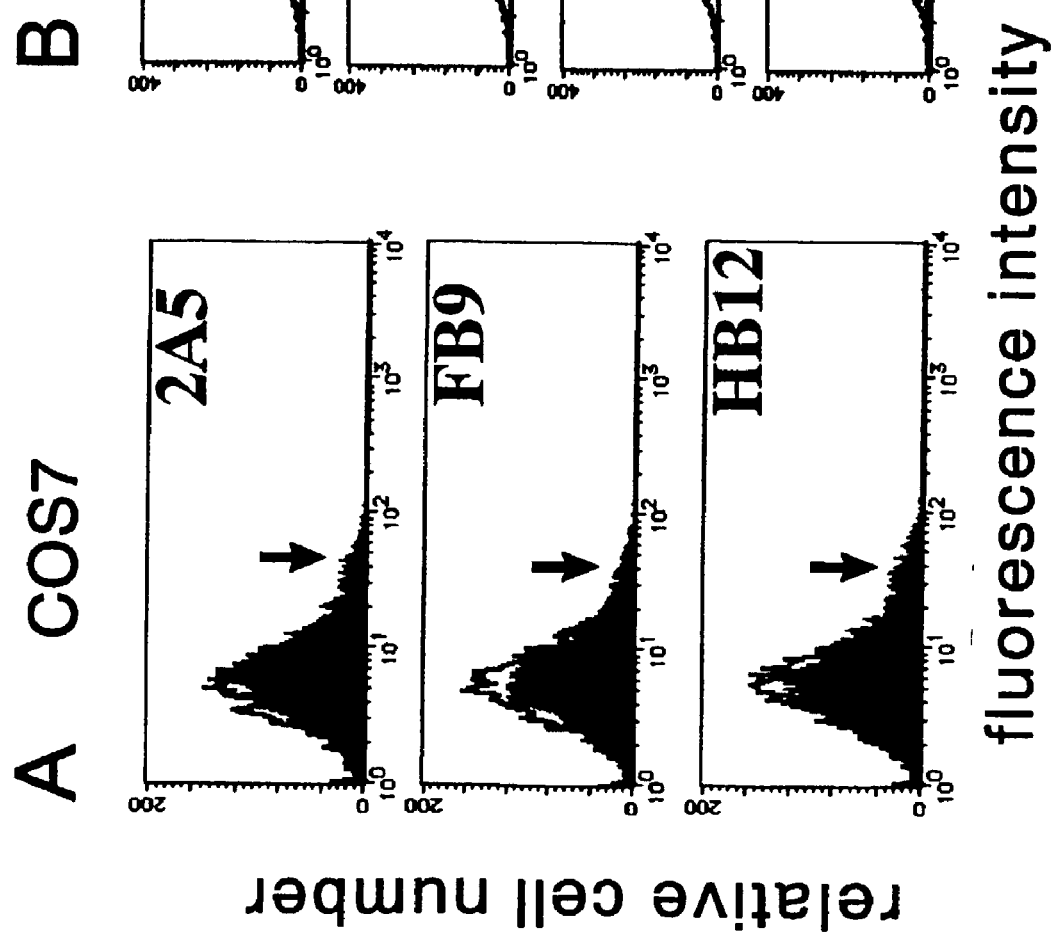
FIGS. 5A and 5B show the graph indicating the results of the flow cytometry in Example 4.

The graphs from the top to the bottom in A in FIG. 5 represent the results of the analysis of the samples employing monoclonal antibodies 2A5, FB9 and HB12 in this order. In each graph, a solid region is the results of the sample obtained from the COS7 cell transfected with the pEF-BOS containing the hST2LcDNA, while an open region is the results of the sample obtained from the COS7 cell transfected with the blank pEF-BOS. As shown in A in FIG. 5, the sample using each monoclonal antibody exhibited a partial right-sided shift of the COS7 cell which had been transfected with the pEF-BOS containing the hST2LcDNA (designated by an arrow in A in FIG. 5).

Subsequently, in order to examine whether a cell which was undergoing an actual in vivo expression of hST2L was capable of being analyzed by a flow cytometry, the experiment similar to that described above was conducted using a human leukemia cell line UT-7/GM cell whose expression of the hST2L in a native condition had been established (Tominaga S., et al.,: Biochem. Biophys. Res. Commun. 14–18: 264, 1999, Komatsu N, et al.,: Blood, 4021–4033: 89, 1997, Yoshida K. et al.,: Hybridoma, 419–427: 14, 1995). Instead of a transfected COS7 cell, the human leukemia cell line UT-7/GM cell was employed. As a control, a sample obtained by using IgG instead of monoclonal antibodies 2A5, FB9 and HB12 was provided. The results of the analysis of each sample by the flow cytometry are shown in B in FIG. 5.

The graphs from the top to the bottom in B in FIG. 5 represent the results of the analysis of the samples employing monoclonal antibodies 2A5, FB9, HB12 and the control IgG in this order. In each graph, a solid region is the results of the sample treated with the FITC-labeled antibodies 2A5, FB9, HB12 and the control IgG, while an open region is the results of the sample without the treatment with such antibodies. As evident from the figure, the cell treated with the monoclonal antibody 2A5 exhibited a marked right-sided shift on the graph, indicating the detection of a specific antigen, while the control IgG exhibited a slight non-specific binding. The cells treated with monoclonal antibodies FB9 and HB12 exhibited the right-sided shift similarly, although the degree was smaller when compared with the monoclonal antibody 2A5. Thus, it was proven to be possible to employ each monoclonal antibody for analyzing an in vivo cell expressing the hST2 by the flow cytometry.

EXAMPLE 5

Preparation and Labelling of Anti-hST2 Polyclonal Antibody (5-1) Immunization and Antiserum Sampling Using the rhST2 obtained in Example 1, a rabbit (Japanese albino rabbit, female, 3.5 kg) was immunized 5 times subcutaneously (about 10 sites, once a week) and a small amount of the blood was taken from a subaural vein and a serum was isolated and examined for the antibody titre by an ELISA method. Thus, the rhST2 was dissolved in $\frac{1}{100}$ M phosphate buffered physiological saline (PBS) to form a 0.1 mg/ml solution, a 100 μl aliquot of which was added to each well of a 96-well microplate "MAXISORP" manufactured by "NUNC", which was allowed to stand at room temperature (20 to 25° C.) for 3 hours. Thereafter, the solution in each well was removed with suction. Subsequently, 30 μl of a PBS containing 5% bovine serum albumin was added and allowed to stand at 4° C. for about 18 hours to block the unreacted region of each well. After discarding the blocking solution, each well was washed three times with 300 μl of the PBS. To each well of the plate thus prepared, 100 μl of a series of an antiserum prepared by a serial dilution of the serum described above with the PBS was added, and allowed to stand at room temperature (20 to 25° C.) for 1 hour. After removing the reaction solution from each well, each well was washed four times with 30 μl of the PBS. Then 100 μl of a diluted peroxidase-labelled anti-rabbit IgG (Medical & Biological Laboratories Co., Ltd.) was added, and allowed to react at room temperature (20 to 25° C.) for 1 hour. Then each well was washed with the PBS as described above, 100 μl of a solution of 3,3',5,5'-tetramethylbenzidine and hydrogen peroxide was added as a chromogenic substrate, and reacted for a certain period. The chromogenic reaction was terminated by adding 1.5 M phosphoric acid to each well, and the absorbance of each well at 450 nm was measured. After ensuring a sufficient antibody titre, 70 ml of the blood was taken from a subaural vein of the rabbit, whereby obtaining about 30 ml of the antiserum.

(5-2) Preparation of Labelled Antibody

From the antiserum described above, an IgG fraction was purified using a DEAE cellulose column. This purified IgG fraction was combined with ficin at 0.056 U per mg IgG, reacted at 37° C. for 8 hours, subjected to a gel filtration through an Ultrogel ACA44, whereby obtaining a F(ab)'2 fraction. This F(ab)'2 fraction was labeled with a peroxidase by a maleimide method to obtain a peroxidase-labeled antibody. The labeling method was in accordance with E. Ishikawa, "ENZYME IMMUNOASSAY, 3rd edition" published by IGAKUSHOIN.

EXAMPLE 6

Construction of ELISA Kit for Quantifying hST2 in Sample (6-1) Selection of Antibody First, in order to construct a sandwich ELISA kit enabling a highly sensitive determination, two types of the antibodies recognizing different sites on the ST2 were selected. Thus, as described in (3-2) in Example 3, the combination of monoclonal antibodies 2A5 and FB9 and the combination of monoclonal antibodies 2A5 and HB12 were selected since monoclonal antibody 2A5 recognized the site on the ST2 which was different from the site recognized by the monoclonal antibody FB9 or HB12. When various assays were performed using these two combinations, it was found that the combination of 2A5 and FB9 gave a lower background absorbance. As a result of a further investigation, the lowest background absorbance was found to be achieved when using the monoclonal antibody FB9 for the capture on the plate and the monoclonal antibody 2A5 for the detection. Therefore, the combination of monoclonal antibodies 2A5 and FB9 was selected and it was decided finally to use the monoclonal antibody FB9 as an antibody for the capture on the plate and the biotinylated monoclonal antibody 2A5 as an antibody for the detection.

(6-2) Preparation of Monoclonal Antibody-Supporting Microplate

An 10 μl aliquot of 100 μl of the monoclonal antibody FB9 dissolved in 0.1 M $Na_2HPO_4$ (pH 9.5) (containing 3 μg of antibody) was added to each well of a 96-well microplate "MAXISORP" manufactured by "NUNC", which was allowed to react at 4° C. for 20 hours. Thereafter, the antibody solution was removed, and 200 μl of a PBS containing 0.1% (w/v) BSA was added to each well, which was allowed to stand at room temperature (20 to 25° C.) for 2 hours to effect the blocking. After discarding the blocking solution, the plate was washed three times with 200 μl of a PBS containing 0.05% (w/v) Tween 20. Then the plate was air-dried to obtain a monoclonal antibody FB9-supporting microplate. The immobilized antibody thus obtained was stored as being sealed tightly together with a desiccant.

EXAMPLE 7

Assay of Soluble ST2 in Sample by Sandwich ELISA Method

A test serum was subjected to a 10-fold dilution with a PBS containing 0.1% (w/v) BSA and a 100 μl aliquot was added to each well of the microplate in (6-2) described above. As a standard, an rhST1 prepared at a desired concentration by diluting with the same buffer was provided, and a 100 μl aliquot was added similarly to the sample. The concentration of the rhST2 was measured by a bradford method using a BSA as a standard.

After allowing the microplate thus prepared to react with agitating gently for 2 hours at room temperature (20 to 25° C.) followed by removing the sample in each well, 30 μl of a PBS containing 0.1% Tween 20 was added to and then removed from each well, whereby washing each well. This washing procedure was performed 5 times. After removing the washing fluid, 50 μl of the biotin-labeled monoclonal antibody 2A5 (400 ng/ml) dissolved in a PBS containing 0.1% (w/v) BSA was added and reacted at room temperature for 2 hours. After washing each well three times as described above, a streptoavidin-HRP conjugate was added to each well and reacted for 30 minutes. After washing four times with the PBS containing 0.1% Tween 20, 100 μl of 10 mM o-phenylenediamine (OPD)-0.01% $H_2O_2$ dissolved in a 50 mM sodium acetate buffer (pH 5.0) was added to each well and reacted for 20 minutes. After the reactions described above, the absorbance of each well at 450 nm was measured using a microplate reader (NIPPON INTERMED).

Figure 6:
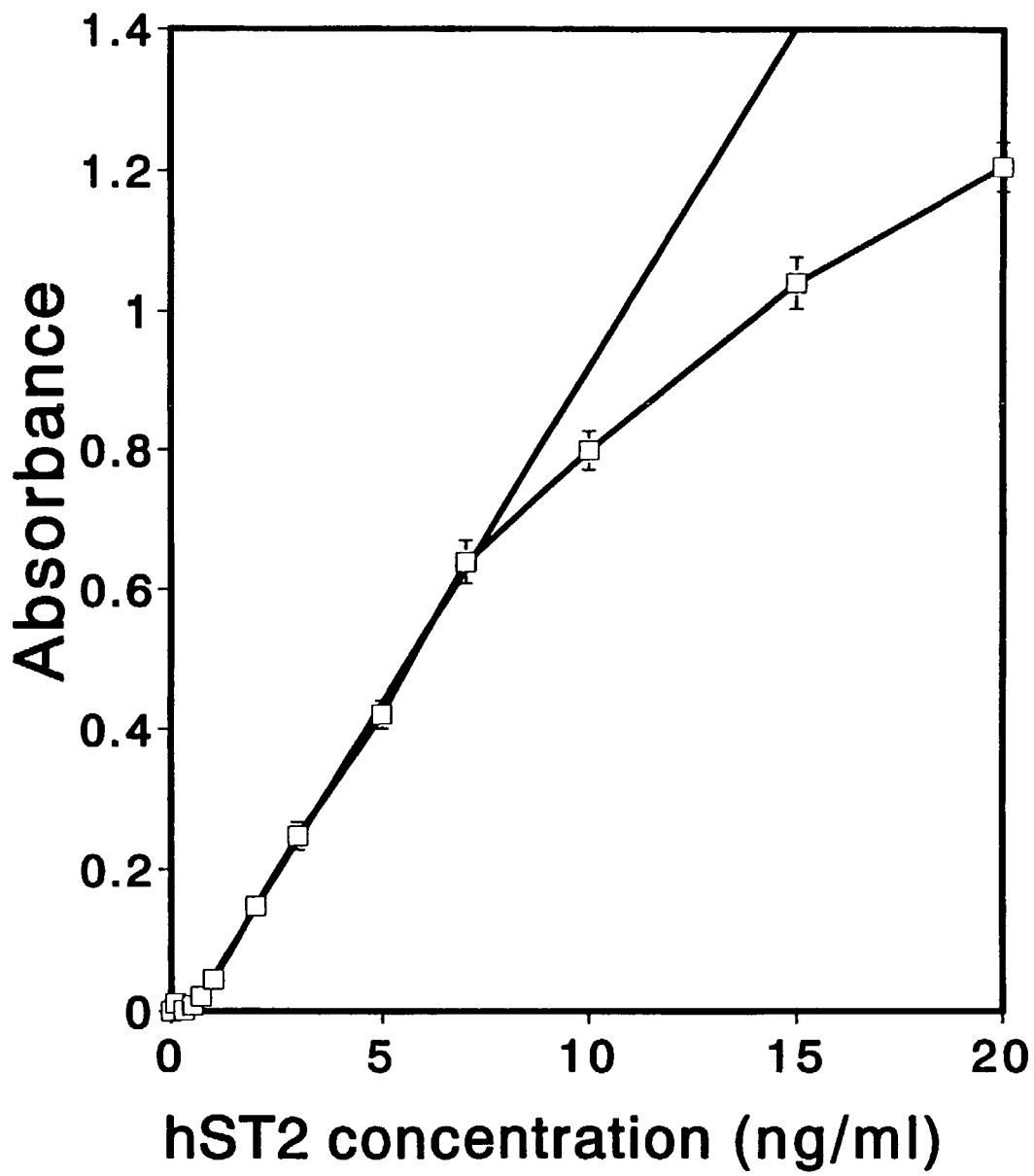
FIG. 6 shows the standard curve obtained by using an rhST1 as a standard which was employed in the quantification by the sandwich ELISA in Example 7.

The graph shown in FIG. 6 is a standard curve prepared using the rhST2 as a standard. Based on this standard curve and the absorbance of a sample, the soluble hST2 in the sample was quantified.

Figure 7:
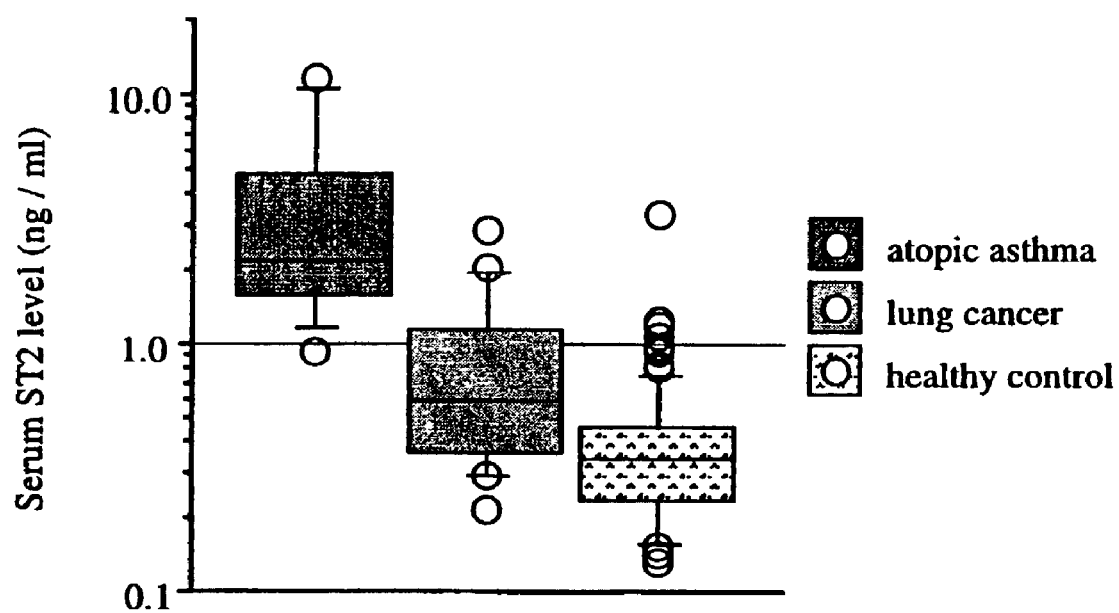
FIG. 7 shows the graph in which the results of the determination of the soluble hST2 in a sample are plotted by disease groups.

Using this assay system, 99 normal volunteers (healthy control), 10 atopic asthma patients (atopic asthma) and 38 lung cancer patients (lung cancer) were examined. Each sample was tested in duplicate. The results are shown in FIG. 7. In FIG. 7, the samples in the atopic asthma group, samples in lung cancer group and samples in healthy control were plotted from left to right in this order. The graph in each group has the 95% confidence interval designated by a square. Similarly, the bar indicates the 90% confidence interval. The data of the samples departing from the 90% confidence interval are designated by open circles.

FIG. 8 shows the number of the cases of each disease and healthy volunteers, mean values, standard deviations and standard errors. Based on the results shown in FIG. 7 and FIG. 8, the level of the soluble ST2 in blood was significantly higher in the atopic asthma group. Thus, by the present inventive assay method, the atopic asthma can be diagnosed rapidly and conveniently.

The present invention is not limited to the above embodiment and examples. A variety of variation aspects are included in the present invention as far as they are not departed from the description of the claims and in a range which can be readily contemplated by those skilled in the art.

According to the invention, an anti-human ST2 monoclonal antibody useful in the detection or measurement of a non-denatured hST2 or membrane-binding hST2L is provided. In addition, a convenient and rapid method for determining a soluble human ST2 using an anti-human ST2 monoclonal antibody is provided. Such a method serves as an effective means for elucidating the functions of the human ST2. Furthermore, an effective means for diagnosing or treating an allergic disease caused by an abnormality in an immune system or an autoimmune disease and the like is also provided. A means useful in the diagnosis especially of an atopic asthma is provided.

What is claimed is:

1. A monoclonal antibody which binds specifically to a non-denatured human ST2 produced by a hybridoma which is designated by deposition number FERM ABP-10190, FERM ABP-10189, or FERM ABP-10191.

2. A hybridoma which produces the monoclonal antibody according to claim 1.

3. A hybridoma having deposition number FERM ABP-10190, FERM ABP-10189, or FERM ABP-10191.

4. A method for determining a soluble human ST2 comprising determining human ST2 in a sample immunologically1 comprising:

contacting said sample with the monoclonal antibody according to claim 1; and determining formation of an immunological complex between the antibody and the ST2 in the sample.

5. An immunological method for determining soluble human ST2, comprising steps a) to c):

a) bringing a sample into contact with an immobilized antibody formed by binding to an insoluble support a first anti-human ST2 antibody which binds specifically to a non-denatured human ST2 to form a first reaction product;

b) labeling said first reaction product by reacting said first reaction product with a second labeled anti-human ST2 antibody which binds specifically to a non-denatured human ST2 by recognizing a site different from a site on ST2 where said first anti-human ST2 antibody binds to form a labeled first reaction product; and, c) determining an amount of label on said labeled first reaction product, the amount of label being indicative of soluble ST2 amount in the sample, wherein said first anti-human ST2 antibody or said second anti-human ST2 antibody is a monoclonal antibody produced by one or more hybridomas selected from the group consisting of hybridomas designated by deposition numbers FERM ABP-10190, FERM ABP-10189, or FERM ABP-10191.

6. The immunological method for determining soluble human ST2 in a sample according to claim 5, further comprising steps d) to g):

d) reacting said immobilized antibody with a soluble human ST2 as a standard to form a second reaction product;

e) labeling said second reaction product by reacting said second reaction product with said second labeled anti-human ST2 antibody to form a labeled second reaction product;

f) preparing a calibration curve by determining the amount of label on said labeled second reaction product; and, g) quantifying soluble human ST2 in said sample from the amount of label on said labeled first reaction product, and said calibration curve.

7. An immunological method for determining a soluble human ST2 according to claim 6 wherein said soluble human ST2 as a standard is a recombinant human ST2.

8. An immunological method for determining soluble human ST2, comprising steps a) to c):

a bringing a sample into contact with an immobilized antibody formed by binding to an insoluble support a first anti-human ST2 antibody which binds specifically to a non-denatured human ST2 to form a first reaction product;

b) labeling said first reaction product by reacting said first reaction product with a second labeled anti-human ST2 antibody which binds specifically to a non-denatured human ST2 by recognizing a site different from a site on ST2 where said first anti-human ST2 antibody binds to form a labeled first reaction product; and, c) determining an amount of label on said labeled first reaction product, the amount of label being indicative of soluble ST2 amount in the sample, wherein said first anti-human ST2 antibody is a monoclonal antibody produced by one or two hybridomas selected from the group consisting of hybridomas designated by deposition numbers FERM ABP-10190, FERM ABP-10189, or FERM ABP-10191, and said second anti-human ST2 antibody is a monoclonal antibody produced by one or two hybridomas which are not selected in said group.

9. An immunological method for determining soluble human ST2, comprising steps a) to c):
   a) bringing a sample into contact with an immobilized antibody formed by binding to an insoluble support a first anti-human ST2 antibody which binds specifically to a non-denatured human ST2 to form a first reaction product;
   b) labeling said first reaction product by reacting said first reaction product with a second labeled anti-human ST2 antibody which binds specifically to a non-denatured human ST2 by recognizing a site different from a site on ST2 where said first anti-human ST2 antibody binds to form a labeled first reaction product; and,
   c) determining an amount of label on said labeled first reaction product, the amount of label being indicative of soluble ST2 amount in the sample.
   wherein said first anti-human ST2 antibody is a monoclonal antibody produced by one or more hybridomas designated by deposition number FERM ABP-10190 or FERM ABP-10191, and said second anti-human ST2 antibody is a monoclonal antibody produced by the hybridoma designated by deposition number FERM ABP-10189.

10. An immunoassay kit for determining a soluble human ST2 comprising a monoclonal antibody which binds specifically to a non-denatured human ST2 produced by a hybridoma which is designated by deposition number FERM ABP-10190, FERM ABP-10189, or FERM ABP-10191.

11. The immunoassay kit according to claim 10 wherein said monoclonal antibody is one or more monoclonal antibodies produced by one or more hybridomas selected from the group consisting of hybridomas designated by deposition numbers FERM ABP-10190, FERM ABP-10189, or FERM ABP-10191.

12. An immunoassay kit for determining soluble human ST2, comprising:
   a first anti-human ST2 antibody which binds specifically to a non-denatured human ST2;
   a second anti-human ST2 antibody which binds specifically to the non-denatured human ST2 by recognizing a site different from the site where said first anti-human ST2 antibody binds and which is labeled with a label; and,
   a soluble human ST2 as a standard,
   wherein said first anti-human ST2 antibody or said second anti-human ST2 antibody is a monoclonal antibody produced by one or more hybridomas selected from the group consisting of hybridomas designated by deposition numbers FERM ABP-10190, FERM ABP-10189, or FERM ABP-10191.

13. The immunoassay kit for determining soluble human ST2 according to claim 12, wherein said soluble human ST2 as a standard is a recombinant human ST2.

14. An immunoassay kit for determining soluble human ST2, comprising:
   a first anti-human ST2 antibody which binds specifically to a non-denatured human ST2;
   a second anti-human ST2 antibody which binds specifically to the non-denatured human ST2 by recognizing a site different from the site where said first anti-human ST2 antibody binds and which is labeled with a label; and,
   a soluble human ST2 as a standard,
   wherein said first anti-human ST2 antibody is a monoclonal antibody produced by one or more hybridomas selected from the group consisting of hybridomas designated by deposition numbers FERM ABP-10190, FERM ABP-10189, or FERM ABP-10191, and wherein said second anti-human ST2 antibody is a monoclonal antibody produced by one or more hybridomas which are not selected in said group.

15. An immunoassay kit for determining soluble human ST2, comprising:
   a first anti-human ST2 antibody which binds specifically to a non-denatured human ST2;
   a second anti-human ST2 antibody which binds specifically to the non-denatured human ST2 by recognizing a site different from the site where said first anti-human ST2 antibody binds and which is labeled with a label; and,
   a soluble human ST2 as a standard,
   wherein said first anti-human ST2 antibody is a monoclonal antibody produced by one or more hybridomas designated by deposition numbers FERM ABP-10190 or FERM ABP-10191, and wherein said second anti-human ST2 antibody is a monoclonal antibody produced by the hybridoma designated by the deposition number FERM ABP-10189.

16. An immunological method for determining soluble human ST2 in a sample, comprising:
   reacting a sample with an immobilized antibody formed by binding to an insoluble support a first monoclonal ST2 antibody produced by a hybridoma designated by deposition number FERM ABP-10190 and which binds specifically to a human ST2 thereby binding human ST2 present in said sample to form bound ST2,
   reacting said bound ST2 with a labeled antibody formed by labeling a second monoclonal antibody produced by a hybridoma designated by deposition number FERM ABP-10189 to form a labeled first reaction product;
   preparing a calibration curve comprising reacting said immobilized antibody with a recombinant human ST2, to form bound standard ST2
   reacting said bound standard ST2 with said labeled antibody to form a labeled second reaction product;
   measuring the amount of label on said labeled second reaction product to produce a calibration curve; and,
   quantifying soluble human ST2 contained in said sample from the amount of label on said first labeled reaction product, and said calibration curve.

17. An immunoassay kit for determining soluble human ST2 comprising:
   an immobilized antibody formed by binding to an insoluble support a first monoclonal antibody which is produced by a hybridoma designated by deposition number FERM ABP-10190 and which binds specifically to a human ST2;
   a labeled antibody formed by labeling a second monoclonal antibody produced by a hybridoma designated by deposition number FERM ABP-10189; and,
   a recombinant ST2 as a standard.

* * * * *

SEQUENCE LISTING

```
<160> NUMBER OF SEQ ID NOS: 2

<210> SEQ ID NO 1
<211> LENGTH: 1357
<212> TYPE: DNA
<213> ORGANISM: Homo sapiens
<300> PUBLICATION INFORMATION:
<301> AUTHORS: Tominaga, S.
      Yokota, T.
      Yanagisawa, K.
      Tsukamoto, T.
      Takagi, T.
      Tetsuka, T.
<302> TITLE: Nucleotide sequence of a complementary DNA for human
      ST2
<303> JOURNAL: Biochim. Biophys. Acta
<304> VOLUME: 1171
<305> ISSUE: 1992
<306> PAGES: 215-218
<308> DATABASE ACCESSION NUMBER: DDBJ/D12763
<309> DATABASE ENTRY DATE: 1992-07-30

<400> SEQUENCE: 1
atctcaacaa cgagttacca atacttgctc ttgattgata aacagaatgg ggttttggat      60
cttagcaatt ctcacaattc tcatgtattc cacagcagca aagtttagta aacaatcatg     120
gggcctggaa aatgaggctt taattgtaag atgtcctaga caaggaaaac ctagttacac     180
cgtggattgg tattactcac aaacaaacaa aagtattccc actcaggaaa gaaatcgtgt     240
gtttgcctca ggccaacttc tgaagtttct accagctgaa gttgctgatt ctggtattta     300
tacctgtatt gtcagaagtc ccacattcaa taggactgga tatgcgaatg tcaccatata     360
taaaaaacaa tcagattgca atgttccaga ttatttgatg tattcaacag tatctggatc     420
agaaaaaaat tccaaaattt attgtcctac cattgacctc tacaactgga cagcacctct     480
tgagtggttt aagaattgtc aggctcttca aggatcaagg tacagggcgc acaagtcatt     540
tttggtcatt gataatgtga tgactgagga cgcaggtgat tacacctgta aatttataca     600
```

-continued

| | |
|---|---|
| caatgaaaat ggagccaatt atagtgtgac ggcgaccagg tccttcacgg tcaaggatga | 660 |
| gcaaggcttt tctctgtttc cagtaatcgg agcccctgca caaaatgaaa taaaggaagt | 720 |
| ggaaattgga aaaacgcaa acctaacttg ctctgcttgt tttggaaaag gcactcagtt | 780 |
| cttggctgcc gtcctgtggc agcttaatgg aacaaaaatt acagactttg gtgaaccaag | 840 |
| aattcaacaa gaggaagggc aaaatcaaag tttcagcaat gggctggctt gtctagacat | 900 |
| ggttttaaga atagctgacg tgaaggaaga ggatttattg ctgcagtacg actgtctggc | 960 |
| cctgaatttg catggcttga gaaggcacac cgtaagacta gtaggaaaaa atccaagtaa | 1020 |
| ggagtgtttc tgagactttg atcacctgaa cttttctctag caagtgtaag cagaatggag | 1080 |
| tgtggttcca agagatccat caagacaatg ggaatggcct gtgccataaa atgtgcttct | 1140 |
| cttcttcggg atgttgtttg ctgtctgatc tttgtagact gttcctgttt gctgggagct | 1200 |
| tctctgctgc ttaaattgtt cgtcctcccc cactccctcc tatcgttggt ttgtctagaa | 1260 |
| cactcagctg cttcttttggt catccttgtt ttctaacttt atgaactccc tctgtgtcac | 1320 |
| tgtatgtgaa aggaaatgca ccaacaaccg aaaactg | 1357 |

<210> SEQ ID NO 2
<211> LENGTH: 2058
<212> TYPE: DNA
<213> ORGANISM: Homo sapiens
<308> DATABASE ACCESSION NUMBER: DDBJ/AB012701
<309> DATABASE ENTRY DATE: 1998-03-31

<400> SEQUENCE: 2

| | |
|---|---|
| aaagagaggc tggctgttgt atttagtaaa gctataaagc tgtaagagaa attggctttc | 60 |
| tgagttgtga aactgtgggc agaaagttga ggaagaaaga actcaagtac aacccaatga | 120 |
| ggttgagata taggctactc ttcccaactc agtcttgaag agtatcacca actgcctcat | 180 |
| gtgtggtgac cttcactgtc gtatgccagt gactcatctg gagtaatctc aacaacgagt | 240 |
| taccaatact tgctcttgat tgataaacag aatggggttt tggatcttag caattctcac | 300 |
| aattctcatg tattccacag cagcaaagtt tagtaaacaa tcatgggggcc tggaaaatga | 360 |
| ggctttaatt gtaagatgtc ctagacaagg aaaacctagt tacaccgtgg attggtatta | 420 |
| ctcacaaaca aacaaagta tcccactca ggaaagaaat cgtgtgtttg cctcaggcca | 480 |
| acttctgaag tttctaccag ctgaagttgc tgattctggt atttatacct gtattgtcag | 540 |
| aagtcccaca ttcaatagga ctggatatgc gaatgtcacc atatataaaa aacaatcaga | 600 |
| ttgcaatgtt ccagattatt tgatgtattc aacagtatct ggatcagaaa aaaattccaa | 660 |
| aatttattgt cctaccattg acctctacaa ctggacagca cctcttgagt ggttttaagaa | 720 |
| ttgtcaggct cttcaaggat caaggtacag ggcgcacaag tcattttttgg tcattgataa | 780 |
| tgtgatgact gaggacgcag gtgattacac ctgtaaattt atacacaatg aaaatggagc | 840 |
| caattatagt gtgacggcga ccaggtcctt cacggtcaag gatgagcaag ctttttctct | 900 |
| gtttccagta atcggagccc ctgcacaaaa tgaaataaag gaagtggaaa ttggaaaaaa | 960 |
| cgcaaaccta acttgctctg cttgttttgg aaaaggcact cagttcttgg ctgccgtcct | 1020 |
| gtggcagctt aatggaacaa aaattacaga ctttggtgaa ccaagaattc aacaagagga | 1080 |
| agggcaaaat caaagtttca gcaatgggct ggcttgtcta gacatggttt taagaatagc | 1140 |
| tgacgtgaag gaagaggatt tattgctgca gtacgactgt ctggccctga atttgcatgg | 1200 |
| cttgagaagg cacaccgtaa gactaagtag gaaaaatcca attgatcatc atagcatcta | 1260 |
| ctgcataatt gcagtatgta gtgtattttt aatgctaatc aatgtcctgg ttatcatcct | 1320 |

-continued

```
aaaaatgttc tggattgagg ccactctgct ctggagagac atagctaaac cttacaagac    1380
taggaatgat ggaaagctct atgatgctta tgttgtctac ccacggaact acaaatccag    1440
tacagatggg gccagtcgtg tagagcactt tgttcaccag attctgcctg atgttcttga    1500
aaataaatgt ggctatacct tatgcattta tgggagagat atgctacctg gagaagatgt    1560
agtcactgca gtggaaacca acatacgaaa gagcaggcgg cacattttca tcctgacccc    1620
tcagatcact cacaataagg agtttgccta cgagcaggag gttgccctgc actgtgccct    1680
catccagaac gacgccaagg tgatacttat tgagatggag gctctgagcg agctggacat    1740
gctgcaggct gaggcgcttc aggactccct ccagcatctt atgaaagtac aggggaccat    1800
caagtggagg gaggaccaca ttgccaataa aaggtccctg aattccaaat tctggaagca    1860
cgtgaggtac caaatgcctg tgccaagcaa aattcccaga aaggcctcta gtttgactcc    1920
cttggctgcc cagaagcaat agtgcctgct gtgatgtgca aagggatctg ggtttgaagc    1980
tttcctgact tctcctagct ggcttatgcc cctgcactga agtgtgagga gcgggaatat    2040
taaagggatt caggccac                                                  2058
```